US008852509B2

(12) United States Patent
Morris et al.

(10) Patent No.: US 8,852,509 B2
(45) Date of Patent: *Oct. 7, 2014

(54) ELECTRONIC DEVICE FOR ANALYZING AQUEOUS SOLUTIONS

(71) Applicant: Hach Company, Loveland, CO (US)

(72) Inventors: David Alexander Nathaniel Morris, Granger, IN (US); Teresa Lynn Swanson, Elkhart, IN (US)

(73) Assignee: Hach Company, Loveland, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/023,672

(22) Filed: Sep. 11, 2013

(65) Prior Publication Data

US 2014/0010728 A1    Jan. 9, 2014

Related U.S. Application Data

(63) Continuation of application No. 11/623,199, filed on Jan. 15, 2007.

(60) Provisional application No. 60/836,322, filed on Aug. 8, 2006.

(51) Int. Cl.
*G01N 33/00*    (2006.01)
*G01N 21/00*    (2006.01)
*G01N 21/47*    (2006.01)
*G01N 31/00*    (2006.01)
*G01N 33/18*    (2006.01)
*G01N 31/22*    (2006.01)
*G01N 21/78*    (2006.01)
*G01N 21/77*    (2006.01)

(52) U.S. Cl.
CPC ............... *G01N 21/78* (2013.01); *G01N 31/00* (2013.01); *G01N 33/18* (2013.01); *G01N 21/77* (2013.01); *G01N 31/22* (2013.01)
USPC ............... 422/68.1; 422/82.05; 422/82.09; 356/446

(58) Field of Classification Search
CPC ....... G01N 15/06; G01N 33/00; G01N 33/18; G01N 33/48; G01N 21/00; G01N 21/47; G01N 21/3577
USPC ................... 422/68.1, 82.05, 82.09; 356/446
See application file for complete search history.

(56) References Cited

U.S. PATENT DOCUMENTS

| | | | |
|---|---|---|---|
| 5,049,487 A | 9/1991 | Phillips et al. | |
| 5,304,468 A | 4/1994 | Phillips et al. | |
| 5,780,304 A | 7/1998 | Matzinger et al. | |
| 5,945,341 A * | 8/1999 | Howard, III | 436/46 |
| 5,965,456 A | 10/1999 | Malmqvist et al. | |

(Continued)

*Primary Examiner* — Lore Jarrett
(74) *Attorney, Agent, or Firm* — Robert L. Wolter, Esq.; Beusse Wolter Sank & Maire, P.A.

(57) ABSTRACT

An electronic device for analyzing an aqueous solution may comprise a housing, one or more measurement circuits and a control circuit all arranged inside the housing. The housing may be configured to receive a test element. The one or more measurement circuits may be configured to produce one or more corresponding sets of measurement signals relating to an aqueous solution received on the test element. The control circuit may include a memory having instructions stored therein that are executable by the control circuit to process the one or more sets of measurement signals to determine one or more corresponding characteristics of the aqueous solution.

21 Claims, 14 Drawing Sheets

(56) References Cited

U.S. PATENT DOCUMENTS

| | | |
|---|---|---|
| 5,965,458 A | 10/1999 | Kouvonen et al. |
| 6,285,454 B1 | 9/2001 | Douglas et al. |
| 6,541,266 B2 * | 4/2003 | Modzelewski et al. ......... 436/95 |
| 6,544,475 B1 | 4/2003 | Douglas et al. |
| 6,602,469 B1 | 8/2003 | Maus et al. |
| 6,979,571 B2 | 12/2005 | Modzelewski et al. |
| 6,986,999 B2 | 1/2006 | Christner et al. |
| 7,488,602 B2 * | 2/2009 | Pachl et al. ................... 436/169 |

* cited by examiner

ELECTRONIC DEVICE FOR ANALYZING AQUEOUS SOLUTIONS

CROSS-REFERENCE TO RELATED U.S. APPLICATION

This application is a Continuation of U.S. application Ser. No. 11/623,199, filed Jan. 15, 2007, which claims the benefit of U.S. Provisional Patent Application No. 60/836,322, filed Aug. 8, 2006, and incorporated herein by reference in their entirety.

FIELD OF THE INVENTION

The present invention relates generally to techniques for analyzing aqueous solutions, and more specifically to electronic devices for determining one or more characteristics of aqueous solutions.

BACKGROUND

Test elements for analyzing aqueous solutions are generally known. For example, test elements for analyzing pool or spa water typically include three chemically treated pads arranged on a substrate; one for measuring free chlorine or bromine concentration, one for measuring pH level and one for measuring total alkalinity of the pool or spa water. To analyze the pool or spa water, such a test element is typically exposed to the pool or spa water, and a chemical reaction then takes place between the chemicals on each of the pads and the pool or spa water. This causes each of the pads to change to a color that is indicative of the corresponding pool or spa water characteristic. The colors of the pads are then typically compared visually to a color chart that maps pad color to a corresponding pool or spa water characteristic.

It is desirable to automate the process of analyzing aqueous solutions, such as for example, but not limited to, pool and spa water, fresh and salt water aquariums, aqueous solutions for medical equipment, and the like. It is accordingly desirable to provide a portable electronic device that automatically conducts such analyses and provides a visual readout of the results.

SUMMARY

The present invention may comprise one or more of the features recited in the attached claims, and/or one or more of the following features and combinations thereof. An electronic device for analyzing an aqueous solution may comprise a portable housing, a measurement circuit and a control circuit. The housing may be configured to receive a test element. The measurement circuit and the control circuit may be arranged inside the housing. The measurement circuit may be configured to produce measurement signals relating to an aqueous solution received on the test element. The control circuit may include a memory having instructions stored therein that are executable by the control circuit to determine a characteristic of the aqueous solution as a function of the measurement signals.

The device may further comprise a display. The control circuit may be operable, according to the instructions, to control the display to display thereon a value of the characteristic of the aqueous solution.

The memory may be configured to store therein at least one value of the characteristic of the aqueous solution.

The memory may have stored therein a model relating the measurement signals to the characteristic of the aqueous solution. The control circuit may be operable, according to the instructions, to process the measurement signals according to the model to determine the characteristic of the aqueous solution. The characteristic of the aqueous solution may be chlorine concentration, and the model may be configured to relate the color signals to chlorine concentration values. Alternatively, the characteristic of the aqueous solution may be bromine concentration, and the model may be configured to relate the color signals to bromine concentration values. Alternatively still, the characteristic of the aqueous solution may be pH level, and the model may be configured to relate the color signals to pH level values. Alternatively still, the characteristic of the aqueous solution may be alkalinity concentration, and the model may be configured to relate the color signals to alkalinity concentration values. Alternatively still, the characteristic of the aqueous solution may be ammonia concentration, and the model may be configured to relate the color signals to ammonia concentration values. Alternatively still, the characteristic of the aqueous solution may be nitrite concentration, and the model may be configured to relate the color signals to nitrite concentration values. Alternatively still, the characteristic of the aqueous solution may be nitrate concentration, and the model may be configured to relate the color signals to nitrate concentration values. Alternatively still, the characteristic of the aqueous solution may be solution hardness, and the model may be configured to relate the color signals to solution hardness values. Alternatively still, the characteristic of the aqueous solution may be peracetic acid concentration, and the model may be configured to relate the color signals to peracetic acid concentration values. Alternatively still, the characteristic of the aqueous solution may be chloramine concentration, and the model may be configured to relate the color signals to chloramine concentration values.

The device may further comprise a switch. The control circuit may be operable, according to the instructions, to be responsive to activation of the switch to process the measurement signals to determine the characteristics of the aqueous solution.

The measurement signals may comprise color signals relating to a color of a portion of the test element resulting from exposure to the aqueous solution. The measurement circuit may comprise a radiation source configured to direct radiation to the color portion of the test element. The control circuit may be operable, according to the instructions, to control activation and deactivation of the radiation source. The radiation source may comprise at least one light emitting diode configured to produce white light. The measurement circuit may comprise a radiation detection circuit configured to detect radiation reflected from the color portion of the test element as a result of radiation thereof by the radiation source, and to produce the color signals based on the detected radiation. The radiation detection circuit may be configured to produce the color signals in the form of a number of color component signals. The number of color component signals may comprise a red color component signal, a green color component signal, a blue color component signal and a white color component signal. The radiation detection circuit may comprise light-to-frequency conversion circuitry configured to produce the color signals in the form of color component signals each in a different range of visible light frequencies.

The device may further comprise a test element placement member attached to the housing. The test element placement member may be configured to receive the test element with a predefined orientation. The device may further comprise a first radiation guide extending between the radiation source and the test element placement member. The first radiation guide may have one open end positioned over the radiation source and an opposite open end. The test element placement member may be configured to receive the test element with a predefined orientation such that the opposite open end of the first radiation guide directs radiation from the radiation source to the color portion of the test element. The device may further comprise a second radiation guide extending between the radiation detection circuit and the test element placement member. The second radiation guide may have one open end positioned over the radiation detection circuit and an opposite end positioned such that radiation reflection from the color portion of the test element, when the test element is received by the test element placement member with the predefined orientation, is directed through the second radiation guide to the one end. The first radiation guide may define a first axis centrally therethrough and the second radiation guide may define a second axis centrally therethrough. The first and second radiation guides may define an angle between the first axis and the second axis. The angle may be an acute angle such as, for example, about 45 degrees.

An electronic device for analyzing aqueous solutions may comprise a portable housing, a plurality of measurement circuits and a control circuit. The plurality of measurement circuits and the control circuit may be arranged inside the housing. The housing may be configured to receive a test element. The plurality of measurement circuits may be configured to produce a corresponding plurality of different sets of measurement signals relating to an aqueous solution received on the test element. The control circuit may include a memory having instructions stored therein that are executable by the control circuit to process each of the plurality of different sets of measurement signals to determine a corresponding plurality of different characteristics of the aqueous solution.

The device may further comprise a display. The control circuit may be operable, according to the instructions, to control the display to display thereon values of the plurality of different characteristics of the aqueous solution.

The memory may be configured to store therein at least one set of values of the plurality of different characteristics of the aqueous solution. The device may further comprise a first switch. The control circuit may be operable, according to the instructions, to be responsive to activation of the first switch to display a set of values of the plurality of different characteristics of the aqueous solution that is stored in the memory. The control circuit may be operable, according to the instructions, to be responsive to multiple activations of the first switch to sequentially display different sets of values of the plurality of different characteristics of the aqueous solution that are stored in memory.

The device may further comprise a second switch. The control circuit may be operable, according to the instructions, to be responsive to activation of the second switch to process each of the plurality of different sets of measurement signals to determine a corresponding plurality of different characteristics of the aqueous solution. The control circuit may be further operable, according to the instructions, to be responsive to activation of the second switch to store values of the plurality of different characteristics of the aqueous solution in the memory.

The memory may have stored therein a plurality of models each relating a different one of the plurality of sets of measurement signals to a corresponding one of the plurality of different characteristics of the aqueous solution. The control circuit may be operable, according to the instructions, to process each of the plurality of sets of measurement signals according to a corresponding one of the models to determine a corresponding one of the plurality of different characteristics of the aqueous solution.

Each of the plurality of measurement circuits may be configured to produce a set of color signals relating to a color of a different portion of the test element resulting from exposure to the aqueous solution. The plurality of different characteristics of the aqueous solution may include chlorine concentration, pH level and alkalinity concentration. The memory may have stored therein first, second and third models. The first model may relate a first set of color signals produced by a first one of the plurality of measurement circuits to chlorine concentration values. The second model may relate a second set of color signals produced by a second one of the plurality of measurement circuits to pH level values. The third model may relate a third set of color signals produced by a third one of the plurality of measurement circuits to alkalinity concentration values.

The plurality of different characteristics of the aqueous solution may include one or more of chlorine concentration, bromine concentration, pH level, alkalinity concentration, ammonia concentration, nitrite concentration, nitrate concentration, solution hardness, peracetic acid concentration, peroxide concentration and chloramine concentration.

A method of analyzing an aqueous solution may comprise exposing a test element to an aqueous solution, producing a first number of color signals corresponding to a color of a first portion of the test element resulting from exposure of the test element to the aqueous solution, and processing values of the first number of color signals according to a first model to determine a first characteristic of the aqueous solution.

The first characteristic may be one of chlorine concentration, bromine concentration, pH level, alkalinity concentration, ammonia concentration, nitrite concentration, nitrate concentration, solution hardness, peracetic acid concentration, peroxide concentration and chloramine concentration.

Producing a first number of color signals may comprise illuminating the first portion of the test element, detecting radiation reflected from the first portion of the test element as a result of illumination thereof, and producing the first number of color signals based on the detected radiation. Producing the first number of color signals based on the detected radiation may comprise producing the first number of color signals in the form of a first number of different color components. The first number of different color components may include red, green, blue and white light components.

The method may further comprise producing a second number of color signals corresponding to a color of a second portion of the test element resulting from exposure of the test element to the aqueous solution, and processing values of the second number of color signals according to a second model to determine a second characteristic of the aqueous solution.

The method may further comprise producing a third number of color signals corresponding to a color of a third portion of the test element resulting from exposure of the test element to the aqueous solution, and processing values of the third number of color signals according to a third model to determine a third characteristic of the aqueous solution. The first characteristic may be chlorine concentration of the aqueous solution. The second characteristic may be pH level of the aqueous solution. The third characteristic may be alkalinity concentration of the aqueous solution.

DESCRIPTION OF THE ILLUSTRATIVE EMBODIMENTS

For the purposes of promoting an understanding of the principles of the invention, reference will now be made to a number of illustrative embodiments shown in the attached drawings and specific language will be used to describe the same.

Figure 1A:
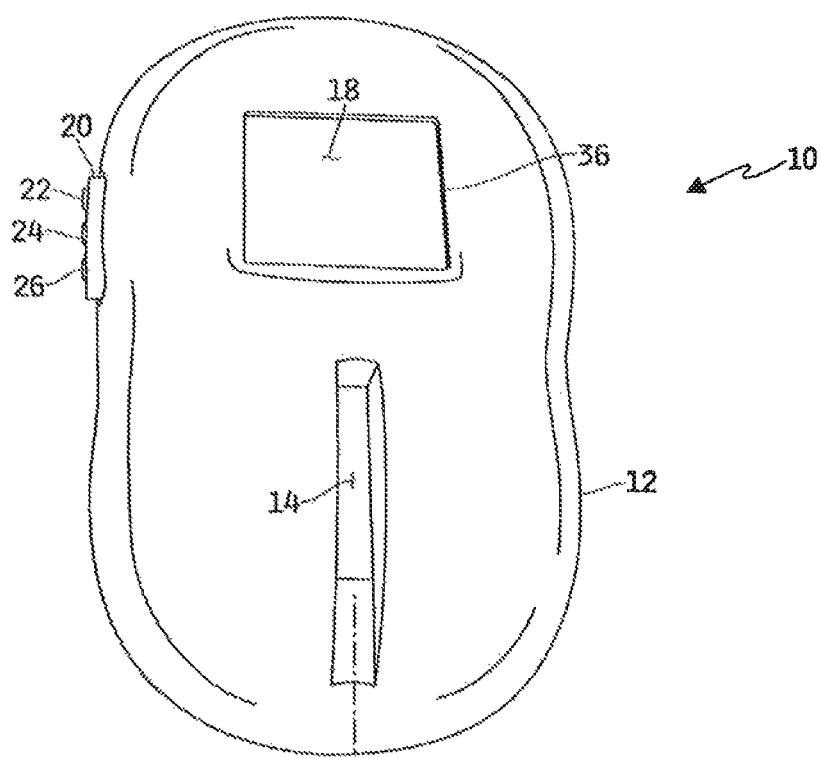
FIG. 1A is a top plan view of an electronic device for analyzing aqueous solutions to which a test element has been exposed.

Referring now to FIG. 1A, a top plan view of an electronic device 10 is shown for analyzing aqueous solutions. In the illustrated embodiment, the electronic device 10 includes a housing 12 defining a test element receiving port 14 configured to receive a test element 16 that has been exposed to an aqueous solution. The housing 12 defines an opening 36 that is sized to expose an electronic display unit 18 that forms part of the electrical circuitry carried by the housing 12. A switch pad or switch member 20 is positioned on one side of the housing 12, and a number of switches 22, 24 and 26 extend from the housing 12 through the switch pad or member 20. The housing 12 may be formed from a conventional molded plastic material, although other materials and/or material compositions are contemplated.

Figure 1B:
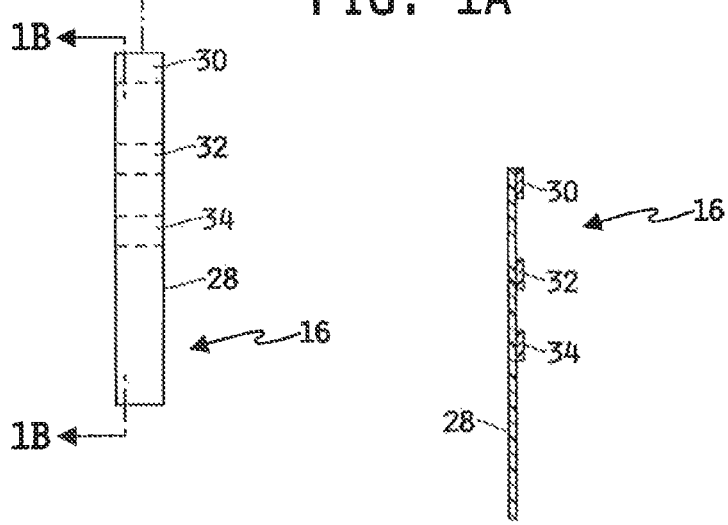
FIG. 1B is a cross-sectional view of the test element of FIG. 1A as viewed along section lines 1B-1B.

Referring now to FIG. 1B, a cross-sectional view of the test element 16 of FIG. 1A, as viewed along section lines 1B-1B, is shown. The test element 16 is conventional in that it is formed of a flexible substrate 28 having a number of pads attached thereto. In the illustrated embodiment, three such pads 30, 32 and 34 are attached to one side of the flexible substrate 28, although more or fewer such pads may alternatively be attached to the substrate 28. Each of the pads 30, 32 and 34 are chemically treated in a conventional manner and with conventional chemical compositions such that each of the pads 30, 32 and 34 react with an aqueous solution when exposed thereto and change to a color that is indicative of a corresponding characteristic of the aqueous solution. In the illustrated embodiment, for example, the test element 16 is a conventional test strip that may be used to test the chlorine or bromine concentration, the pH level and total alkalinity of pool or spa water. In this example, one of the chemically treated pads, e.g., pad 30, is chemically treated such that it will change color, when exposed to an aqueous solution that is indicative of chlorine or bromine concentration of the aqueous solution. The pads 32 and 34 are likewise chemically treated such that one of the pads, e.g., pad 32 will change, when exposed to an aqueous solution, to a color that is indicative of a pH level of the aqueous solution, and the other pad, e.g., pad 34, will change, when exposed to the aqueous solution, to a color that is indicative of the total alkalinity of the aqueous solution.

To analyze the pool or spa water, the test element 16 is typically exposed to the pool or spa water, and a chemical reaction then takes place between the chemicals on each of the pads 30, 32 and 34 and the pool or spa water. This causes each of the pads to change to a color that is indicative of the corresponding pool or spa water characteristic, as just described. The colors of the pads 30, 32 and 34 are then typically compared visually to a color chart that maps pad color to a corresponding pool or spa water characteristic. The color chart may, for example, be imprinted on, or attached to, a container or vessel in which the test elements are supplied. Typically ideal ranges for pools and spas are 1-3 ppm of chlorine (or 3-6 ppm of bromine), 80-120 ppm total alkalinity, and 7.2-7.6 pH, and in this exemplary embodiment the pads 30, 32 and 34 are chemically treated in a conventional manner and with conventional chemical compositions to provide for detection of chlorine or bromine, total alkalinity and pH in these ranges. It will be appreciated, however, that the pads may alternatively or additionally be chemically treated to provide for detection of such characteristics in other ranges. The pads themselves may be formed of any bibulous material, and one example of such a bibulous material that may be used to form the pads 30, 32 and 34 is, but should not be limited to, filter paper.

The test elements 16 just described are conventionally provided with a substrate 28 that is white in color to provide a neutral background for visually comparing the colors of the pads 30, 32 and 34 to a color chart as just described. In the embodiment illustrated in FIGS. 1A and 1B, the test element 16 differs from such conventional test elements in that the substrate 28 is configured to minimize, or at least reduce, radiation reflection to facilitate analysis of the test element 16 by the electronic device 10. In one specific embodiment, for example, the substrate 28 is black in color.

For purposes of this disclosure, the electronic device 10 will be described herein as being configured to determine the colors of the pads 30, 32 and 34 of the test element 16 illustrated in FIGS. 1A and 1B, and to determine and display on the display unit 18 numerical values of the corresponding chlorine (or bromine), alkalinity and pH levels of an aqueous solution to which the test element 16 has been exposed. It will be understood, however, that the test element 16 may alternatively have more or fewer such pads attached thereto, and/or be chemically treated with alternative chemical compositions configured to change color as a function of one or more different characteristics the aqueous solution. Examples of such alternative characteristics of the aqueous solution to which at least one pad arranged on the substrate 28 may be sensitive to include, but are not limited to, ammonia concentration, nitrite concentration, nitrate concentration, solution hardness, peracetic acid concentration, and chloramine concentration.

Figure 2:
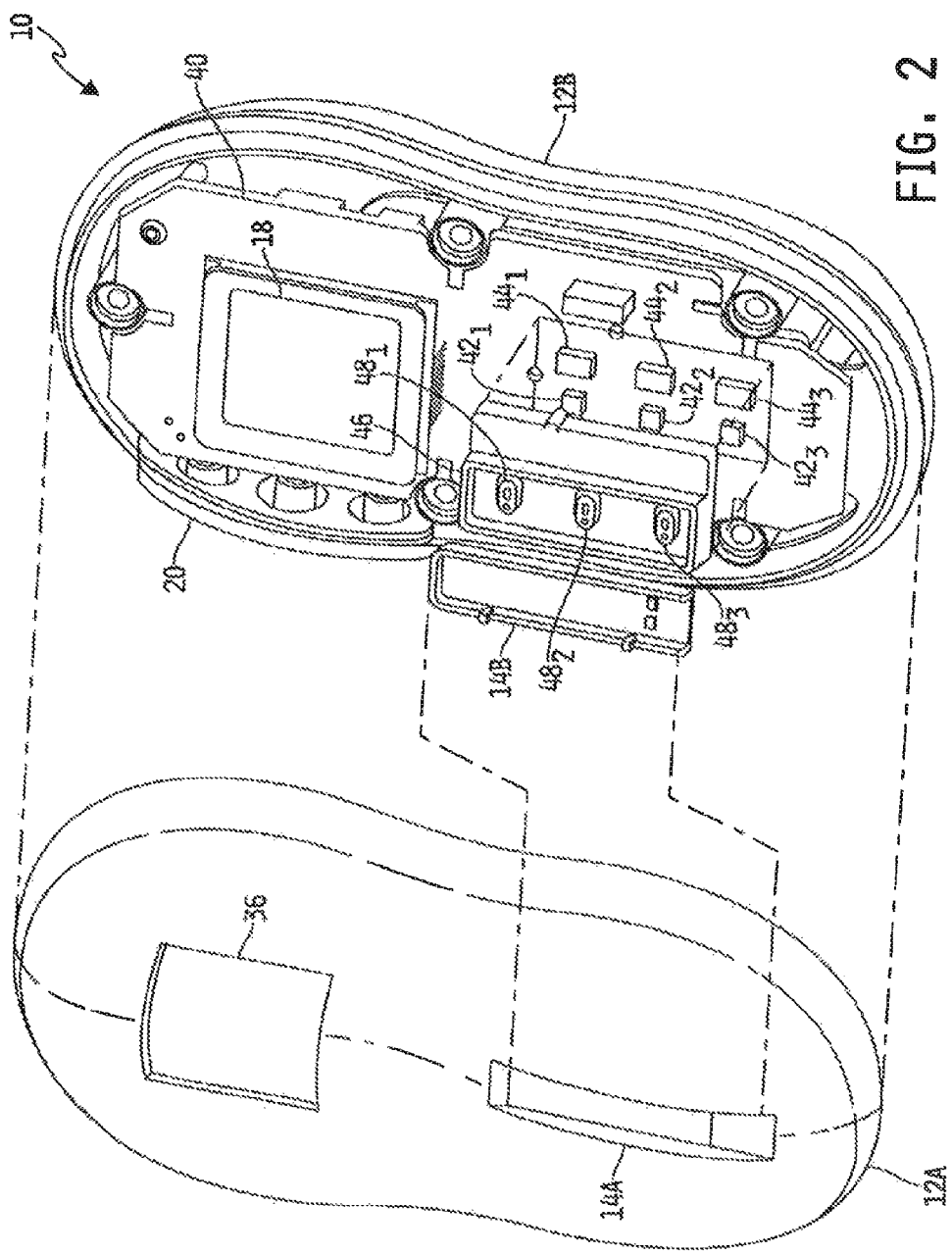
FIG. 2 is a partial assembly view of the device shown in FIG. 1A for analyzing aqueous solutions.

Referring now to FIG. 2, a partial assembly view of the electronic device 10 for analyzing aqueous solutions is shown. In the illustrated embodiment, the housing 12 is shown as having a top portion or cover 12A and a bottom portion 12B. The top portion or cover 12A defines the opening 36 through which the display unit 18 is visible and further defines a slot 14A that defines, in part, the test element receiving port 14 of FIG. 1A. A test element placement member 14B is configured to be attached to the underside of the top portion or cover 12A of the housing 12, and juxtaposed with the slot 14A such that a test element 16 received in the slot 14A is received on the test element placement member 14B. Together, the slot 14A and the test element placement member 14B define the test element receiving port 14.

The bottom portion 12B of the housing 12 is sized to receive therein a circuit board 40 having the electronic display unit 18, as well as a number of additional electrical components, mounted thereto. The additional electrical components include, for example, a number of conventional radiation detection circuits and a corresponding number of conventional radiation sources. Generally, the number of radiation sources and radiation detection circuits will correspond to the number of pads arranged on the test element 16. In the embodiment illustrated in the attached drawings, for example, the test element 16 has three such pads 30, 32 and 34 mounted thereto, and the circuit board 40 in this embodiment accordingly has three radiation sources $42_1$-$42_3$ mounted thereto and three corresponding radiation detection circuits $44_1$-$44_3$ also mounted thereto. A radiation guide structure 46 defines three corresponding radiation guides members $48_1$-$48_3$, wherein the radiation guide structure 46 is configured to be received on the circuit board 40 such that each radiation guide member $48_1$-$48_3$ is aligned with a corresponding pair of the radiation sources $42_1$-$42_3$ and radiation detection circuits $44_1$-$44_3$, and such that the top surfaces of all of the radiation guide members $48_1$-$48_3$ are juxtaposed with a bottom surface of the test element placement member 14B when the top portion or cover 12A engages the bottom portion 12B.

Figure 3:
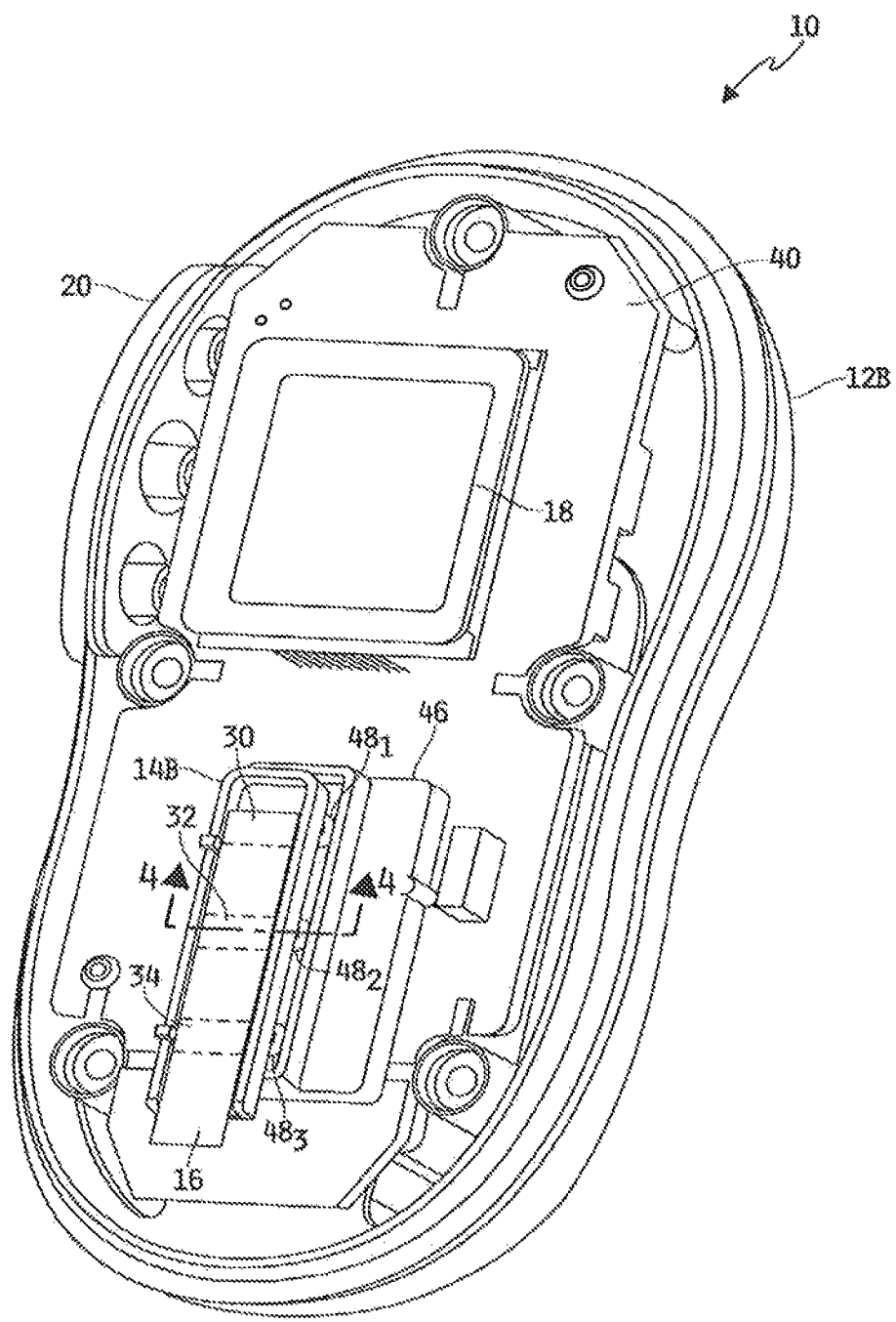
FIG. 3 is an assembled view of a portion of the device shown FIG. 2 further illustrated with a test element operatively received by the device.

Referring now to FIG. 3, an assembled view of the bottom portion 12B of the housing 12 is shown with the circuit board 40 mounted thereto and with the radiation guide structure 46 positioned over the radiation sources $42_1$-$42_3$ and radiation detection circuits $44_1$-$44_3$. The test element placement member 14B is shown in FIG. 3 as being juxtaposed over the radiation guide structure 46 as it would be when the top portion or cover 12A of the housing 12 is mounted to the bottom portion 12B. A test element 16 is superimposed onto FIG. 3 to illustrate that when the test element 16 is received on the test element placement member 14B with the illustrated and predefined orientation, the pads 30, 32 and 34 arranged on the test element 16 are juxtaposed over corresponding ones of the radiation guide members $48_1$-$48_3$. Radiation emitted by the radiation sources $42_1$-$42_3$ is guided by corresponding ones of the radiation guide members $48_1$-$48_3$ to direct the emitted radiation to corresponding ones of the pads 30, 32 and 34 of the test element 16, and to also direct the resulting radiation reflected by each of the pads 30, 32 and 34 to corresponding ones of the radiation detection circuits $44_1$-$44_3$. Signals produced by the radiation detection circuits $44_1$-$44_3$ in response to the reflected radiation are then used to determine the different colors of the pads 30, 32 and 34 that result from exposure of the test element 16 to an aqueous solution, as will be described in greater detail hereinafter.

Figure 4:
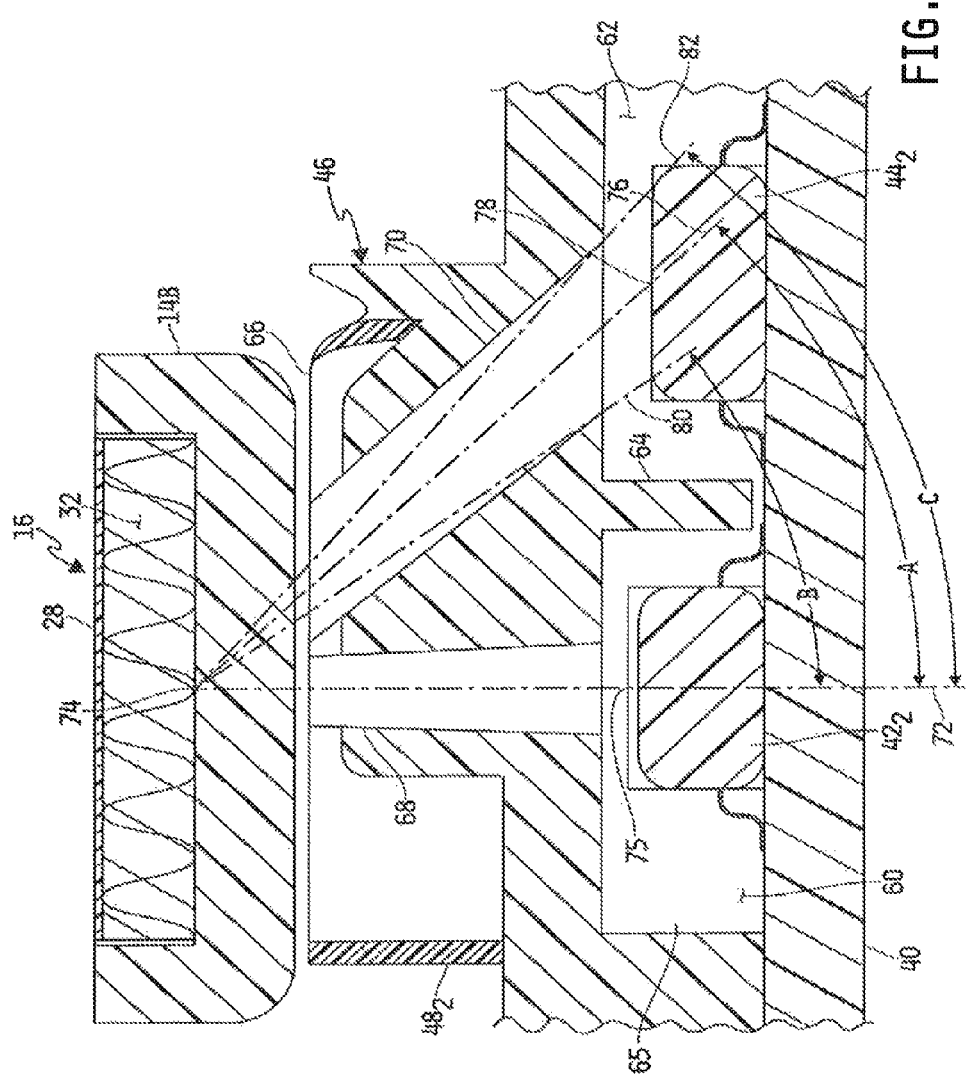
FIG. 4 is a cross-sectional view of a portion of the device of FIG. 3 viewed along section lines 4-4.

Referring now to FIG. 4, a cross-section of the radiation guide structure 46, the test element placement member 14B and the test element 16 is shown as viewed along section lines 4-4 of FIG. 3. In the illustrated embodiment, the radiation source $42_2$ and the radiation detection circuit $44_2$ are shown as being mounted to the circuit board 40. The radiation guide member $48_2$ defines a first cavity 60 and a second cavity 62 with a wall 64 defined between the two cavities 60 and 62. The cavities 60 and 62 are sized to receive the radiation source $42_2$ and the radiation detection circuit $44_2$ respectively therein when the radiation guide structure 46 is positioned on the circuit board 40 as illustrated in FIGS. 2 and 3. The wall 64 separates the cavities 60 and 62 to minimize radiation transmission therebetween. An outer wall 65 surrounds and encloses the cavities 60 and 62 to define the radiation guide member $48_2$.

The radiation guide member $48_2$ defines a radiation guide in the form of a passageway 68 that extends between the cavity 60 and a top portion 66 of the radiation guide member $48_2$. The passageway 68 is an open passageway having one end open to the cavity 60 and an opposite end defining an opening in the top portion 66 of the radiation guide member $48_2$. The radiation guide member $48_2$ defines another radiation guide 70 therethrough in the form of another passageway extending between the top portion 66 of the radiation guide member $48_2$ and the cavity 62. The passageway 70 is an open passageway having one end open to the cavity 62 and an opposite end defining an opening in the top portion 66 of the radiation guide member $48_2$. In the illustrated embodiment, the radiation guides 68 and 70 are circular in cross-section, although other cross-sectional shapes of the radiation guides 68 and 70 are contemplated.

The radiation guide 68 defines a longitudinal axis 72 extending centrally therethrough. In the illustrated embodiment, the longitudinal axis 72 defined by the radiation guide 68 extends through approximately a central portion of the radiation source $42_2$ and also through approximately a central portion of the test element placement member 14B at a location corresponding to a center point 74 of the pad 32 of a test element 16 when the test element 16 is received on the test element placement member 14B with the predefined orientation relative to the test element placement member 14B. The radiation guide 70 similarly defines a longitudinal axis 76 extending centrally therethrough. In the illustrated embodiment, the longitudinal axis 76 defined by the radiation guide 70 extends through approximately a central portion of the radiation detection circuit $44_2$ and also through the test element placement member 14B at a location such that the longitudinal axis 76 bisects the axis 72 at approximately the center point 74 of the pad 32 of the test element 16. It will be appreciated that the radiation guides 68 and 70 may be alternatively positioned relative to the test element placement member 14B, or vice versa, such that the bisection point of the longitudinal axes 72 and 76 is positioned at any desired location of the pad 32. Likewise, either or both of the radiation guides 68 and 70 may be alternatively positioned relative to the cavities 60 and 62 respectively such that the axis 72 extends non-centrally through the radiation source 42$_2$ and/or that the axis 76 extends non-centrally through the radiation detection circuit 44$_2$.

The side wall of the radiation guide 70 defines boundary axes 80 and 82 extending from the bisection point of the axes 72 and 76 to opposing locations of the side wall at the opening of the radiation guide 70 adjacent to the cavity 62, as illustrated in FIG. 4. The longitudinal axes 72 and 76 define an angle, A, therebetween, the longitudinal axis 72 and the boundary axis 80 of the radiation guide 70 define another angle, B, therebetween, and the longitudinal axis 72 and the other boundary axis 82 of the radiation guide 70 define yet another angle, C, therebetween. The angles A, B and C are typically selected such that the longitudinal axis 72 defined through the radiation guide 68 extends through a substantially central point 75 defined on the top surface of the radiation source 42$_2$, the longitudinal axis 76 defined through the radiation guide 70 extends through a substantially central point 78 defined on the top surface of the radiation detection circuit 44$_2$, and the boundary axes 80 and 82, extend through a top portion of the radiation detection circuit 44$_2$ adjacent to the sides of the radiation detection circuit 44$_2$. With this arrangement, radiation emitted by the radiation source 42$_2$ extends through the radiation guide 68 to the pad 32 of the test element 16, and is reflected from the pad 32 of the test element 16 through the radiation guide 70 and onto the top surface of the radiation detection circuit 44$_2$. In one exemplary embodiment, the angle, A, is approximately 45°, the angle, B, is approximately 37.73°, and the angle, C, is approximately 50.804°, although other angles of A, B and C are contemplated.

Radiation emitted by the radiation source 42$_2$ passes through the radiation guide 68, through the test element placement member 14B and strikes the surface of the pad 32 that is arranged on the substrate 28 of the test element 16. Radiation is then reflected from the surface of the pad 32 and extends through the radiation guide 70 through the top surface 78 of the radiation detection circuit 44$_2$. The test element placement member 14B is accordingly formed of a material that is radiation transmissive, particularly in the frequency range of the radiation source 44$_2$. The radiation guide member 48$_2$ is conversely formed of a material that does not transmit radiation therethrough so that the radiation may be confined by the radiation guides 68 and 70. In one illustrative embodiment, the radiation guide structure 46 is formed of pigmented nylon and the test element placement member 14B is formed of black polycarbonate although other materials and/or material compositions are contemplated for either structure.

It will be understood that while operation of the radiation guide structure 46 was described hereinabove with respect to the radiation guide member 48$_2$, any additional radiation guide members defined by the radiation guide structure 46, e.g., radiation guide members 48$_1$ and 48$_3$, operate identically with respect to corresponding pairs of radiation sources and radiation detection circuits.

Figure 5:
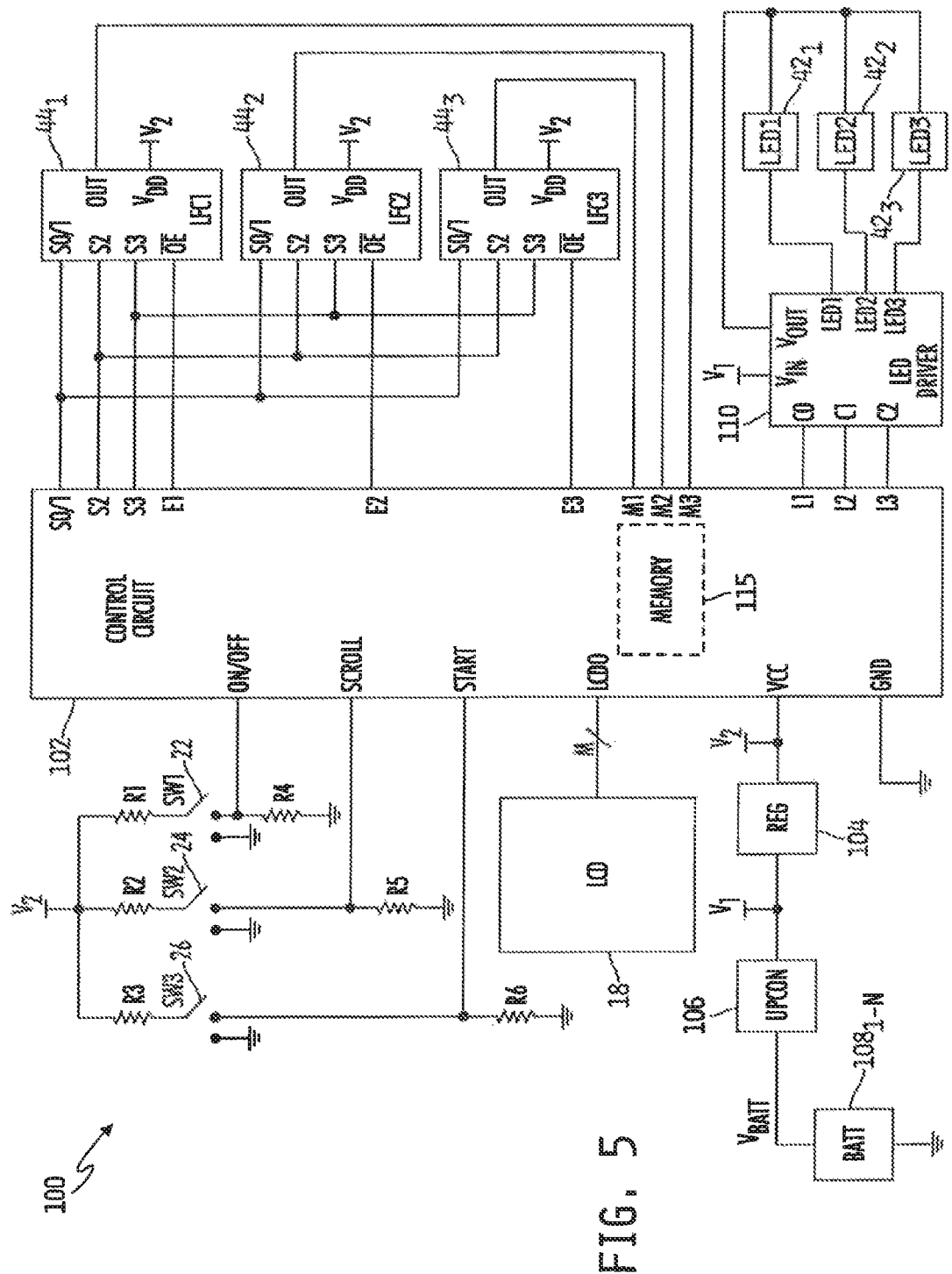
FIG. 5 is a schematic diagram illustrating some of the electrical circuitry mounted to the circuit board of FIGS. 2 and 3.

Referring now to FIG. 5, a schematic diagram is shown of one illustrative embodiment of some of the electrical circuitry 100 mounted to the circuit board 40 illustrated in FIGS. 2 and 3. The electrical circuitry 100 generally manages the overall operation of the electronic device 10, including determining one or more characteristics of an aqueous solution to which a test element 16 has been exposed. In the illustrated embodiment, a control circuit 102 is configured to control operation of the electronic device 10. The control circuit 102 has, or has access to, a memory unit 115. The memory unit 115 has stored therein one or more software processes that are executable by the control circuit 102 to determine one or more characteristics of an aqueous solution to which the test element 16 has been exposed, as a function of measurement signals produced by one or more corresponding radiation detection circuits. In the illustrated embodiment, three such radiation detection circuits 44$_1$-44$_3$ are shown, and in this embodiment the electronic device 10 is configured to determine three characteristics of an aqueous solution to which the test element 16 has been exposed. It will be understood, however, that the electronic device 10 may include more or fewer such radiation detection circuits and the control circuit 102 may be configured as described herein to control any such number of radiation detection circuits to determine any corresponding number of characteristics of an aqueous solution to which the test element 16 has been exposed.

The control circuit 102 includes a VCC input receiving a regulated voltage, V2, produced at an output of a conventional voltage regulator circuit 104, and a GND terminal that is connected to a reference potential, e.g., ground potential. The voltage regulator circuit 104 has an input receiving a voltage, V1, produced at an output of a conventional voltage up-converter circuit 106. The voltage up-converter circuit 106 has an input receiving a battery voltage, $V_{BATT}$, produced by any number, N, of conventional batteries 108$_1$-108$_N$, wherein N may be any positive integer. Illustratively, the number N of batteries may be provided in the form of one or more conventional dry-cell batteries that may or may not rechargeable in a conventional manner. In one exemplary embodiment, for example, the circuit 100 may include two or more conventional dry-cell batteries connected to produce a battery voltage, $V_{BATT}$, of about 3.0 volts. In this embodiment, the voltage up-converter circuit 106 may be, for example, a conventional step-up DC-DC converter configured to step-up the battery voltage, $V_{BATT}$, of approximately 3.0 volts to an output voltage, V1, of approximately 5.0 volts. In one specific embodiment, for example, the voltage up-converter circuit may be a MAX1674EUA step-up DC-DC converter circuit produced by Maxim Integrated Products. The voltage regulator circuit 104, in this exemplary embodiment, may be, for example, a SP6201EM5-L-3.3/TR voltage regulator produced by Sipex Corporation. In this exemplary embodiment, the battery voltage, $V_{BATT}$, is approximately 3.0 volts nominal, the up-converter voltage V1, is approximately 5.0 volts, and the regulated voltage V2, is also about 5.0 volts, although it will be understood that the present disclosure contemplates other values of $V_{BATT}$, V1 and V2 and any conventional electronic circuitry necessary to produce such voltages.

The circuitry 100 further includes a conventional display device 18, as described hereinabove, having a number, M, of inputs that are electrically connected to a corresponding number, M, of outputs of the control circuit 102, where M may be any positive integer. In the illustrated embodiment, the display device 18 is provided in the form of a conventional liquid crystal display (LCD), one example of which is a conventional 67 segment, 3-MUX LCD unit having 24 data inputs and three control inputs. It will be understood, however, that the display device 18 may be provided in the form of other conventional LCD display units or alternatively in the form of one or more other conventional display units including, but not limited to, one or more LED display units, one or more vacuum-fluorescent display units, or the like.

The control circuit 102 further has an on/off input that is electrically connected to one terminal of the switch 22 and also to one end of a resister, R4, having an opposite end electrically connected to ground potential. Another terminal of the switch 22 is electrically connected to one end of a resister, R1, the opposite end of which is electrically connected to the potential V2. Yet another terminal of the switch is connected to ground potential. The control circuit 102 is response to the "on" state of the switch 22, e.g., when the ends of the resistors R1 and R4 are electrically connected together by the switch 22, to power up to an operational state and to activate at least some of the electrical components of the electrical circuitry 100. The control circuit is responsive to the "off" state of the switch 22, e.g., when the end of the resistor R4 is connected by the switch 22 to ground potential, to power down or enter a conventional low-power "sleep" mode, and to deactivate at least some of the electrical components of the electronic circuitry 100.

The control circuit 102 further includes a scroll input which is electrically connected to one terminal of the switch 24 and also to one end of a resister, R5, having an opposite end that is electrically connected to ground potential. Another terminal of the switch 24 is electrically connected to one end of a resister, R2, having an opposite end electrically connected to the potential V2. Yet another terminal of the switch 24 is electrically connected to ground potential. The control circuit 102 is responsive to a first activation of the "on" state of the scroll switch 24, e.g., when the two ends of the resistors R2 and R5 are electrically connected together by the switch 24, to display on the display unit 18 a previous set of aqueous solution characteristics that is stored in the memory unit 115, as will be described in greater detail hereinafter. The control circuit 102 is further responsive to successive activations of the "on" state of the scroll switch 24 within predefined time periods of each other to display on the display unit 18 previous sets of aqueous solution characteristics that have been stored in the memory unit 115, as will also be described hereinafter. The control circuit 102 is illustratively configured to take no action when the switch 24 is in the "off" state, e.g., when the resistor R2 is electrically connected by the switch 24 to ground potential.

The control circuit 102 further includes a START input that is electrically connected to one terminal of the switch 26 and also to one end of a resister, R6, having an opposite end that is electrically connected to ground potential. Another terminal of the switch 26 is electrically connected to one end of a resister, R3, having an opposite end that is electrically connected to the potential V2. Yet another terminal of the switch 26 is electrically connected to ground potential. The control circuit 102 is responsive to the "on" state of the switch 26, e.g., when the resistors R3 and R6 are electrically connected together by the switch 26, to begin processing a test element 16 that has been received on the test element placement member 14B to determine one or more characteristics of an aqueous solution to which the test element 16 has been exposed, as will be described in greater detail hereinafter. The control circuit 102 is illustratively configured to take no action when the switch 26 is in the "off" state, e.g., when the resistor R3 is electrically connected by the switch 26 to ground potential.

The electrical circuitry 100 further includes a number of radiation sources, as well as circuitry that is controllable by the control circuit 102 to activate and deactivate such radiation sources. In the embodiment illustrated in FIG. 5, the number of radiation sources are implemented in the form of three light emitting diodes (LEDs) that are each electrically connected to a conventional LED driver circuit 110 that is itself electrically connected to the control circuit 102. Illustratively, the LED driver circuit 110 may be provided in the form of a CAT3604-channel white LED driver manufactured by Catalyst Semi-Conductor, Inc., and each of the radiation emitting diodes $42_1$-$42_3$ are provided in the form of conventional LEDs configured to produce white light. It will be understood, however, that other radiation sources configured to produce radiation in any desired frequency range are contemplated, as well as any supporting circuitry that may be necessary to drive any such alternative radiation sources.

In the embodiment illustrated in FIG. 5, LED outputs, L1-L3, of the control circuit 102 are each electrically connected to corresponding control inputs, C0-C2, of the LED driver circuit 110. A supply voltage input, $V_{IN}$, of the LED driver circuit 110 receives the voltage V1 produced by the up-converter circuit 106. The LED driver circuit 110 includes a charge pump that boosts the voltage V1 to an output voltage, $V_{out}$, suitable for achieving a nominal LED current. The output, $V_{OUT}$, of the LED driver circuit 110 is electrically connected to the anodes of each of the LEDs, $42_1$-$42_3$, and the cathodes of each of the LEDs, $42_1$-$42_3$, are electrically connected to corresponding LED inputs, LED1-LED3, of the LED driver circuit 110. In this embodiment, the LED driver circuit 110 includes a number of dedicated current sink regulators each connected to a corresponding one of the LED inputs, LED1-LED3, and each of which are controllable according to the activation state of the control inputs C0-C2, to thereby control activation and deactivation of the LEDs, $42_1$-$42_3$. In the illustrated embodiment, for example, all of the LEDs, $42_1$-$42_3$, are in the off (non-illuminating) states when each of the control inputs, C0-C2, are controlled to a logic high state. The first LED, $42_1$, may be activated (illuminated) by controlling either or both of the inputs C0 and C1 to a logic low state and the input C2 to a logic high state or by controlling both of the inputs C0 and C1 to logic low states and the input C2 to a logic low state, the second LED, $42_2$, can be activated (illuminated) by controlling either or both of the inputs C0 and C1 to a logic low state and the input C2 to a logic high state or by controlling the input C0 to a high logic high state, controlling the input C1 to a logic low state and controlling the input C2 to a logic low state, and the third LED, $42_3$, can be activated (illuminated) by controlling either, but not both, of the inputs C0 and C1 to a logic low state and the input C2 to a logic high state or by controlling the input C0 to a logic low state, the input C1 to a logic high state and controlling the input C2 to a logic low state.

It will be appreciated that other conventional LED driver circuits can be used to control operation of the LEDs, $42_1$-$42_3$, via the control circuit 102. It will further be appreciated that one or more of the radiation sources $42_1$-$42_3$ may be configured to emit radiation in other visible frequency ranges and/or in non-visible frequency ranges. The driver circuit 110 will, in any such case, be provided in the form of one or more conventional driver circuits configured to control activation and deactivation of the one or more radiation sources based on any number of control signals provided thereto by the control circuit 102.

The electronic circuitry 100 further includes a number of radiation detection circuits as described hereinabove with respect to FIGS. 1A and 2-4. In the embodiment illustrated in FIG. 5, three such radiation detection circuits, $44_1$-$44_3$, are provided in the form of conventional radiation detection circuits each configured to produce a number of measurement signals corresponding to radiation reflected thereon from one of the chemically treated pads 30, 32 or 34 of the test element 16 as a result of being irradiated by a corresponding one of the radiation sources. In one specific embodiment wherein the one or more radiation sources are provided in the form of LEDs configured to irradiate visible light, e.g., white light, the radiation detection circuits $44_1$-$44_3$ are each provided in the form of a TCS230D TR color light-to-frequency converter circuit manufactured by Texas Advanced Optical Electronic Solutions, Inc. In this embodiment, select outputs S0/1, S2 and S3 of the control circuit 102 are each electrically connected to corresponding select inputs, S0/1, S2 and S3 of each of the radiation-to-frequency converter circuits $44_1$-$44_3$, where S0/1 denotes two inputs S0 and S1 that are connected together externally to the circuits $44_1$-$44_3$. Additionally, three enable outputs, E1-E3, of the control circuit 102 are connected to output enable inputs, OE, of a different one of each of the light-to-frequency converter circuits $44_1$-$44_3$, Outputs, OUT, of each of the light-to-frequency converter circuits, $44_1$-$44_3$, are electrically connected to corresponding measurement signal inputs, M1-M3, of the control circuit 102. Each of the light-to-frequency converter circuits, $44_1$-$44_3$, includes an array of photodiodes arranged on the top surface thereof, and a current-to-frequency converter configured to produce an output signal in the form of a square wave signal having a frequency that is directly proportional to the intensity of radiation detected by the array of photodiodes. Illustratively, the array of photodiodes includes 16 photodiodes having blue filters, 16 photodiodes having green filters, 16 photodiodes having red filters, and 16 photodiodes having no filters, e.g., that are clear. All photodiodes of the same color are electrically connected in parallel, and can be separately activated as a function of logic states of the selection inputs S2 and S3. For example, with S2 and S3 both in a logic low state, the red photo diodes are active, with S2 in the low logic state and S3 in the high logic state, the blue photo diodes are active, with S2 in the high logic state and S3 in the low logic state, the clear (no filter) photo diodes are active, and with S2 and S3 both in the logic high state, the green photo diodes are active.

The light-to-frequency converter circuits, $44_1$-$44_3$, are in a powered down state when the S0/1 inputs are both in a logic low state, and are configured to provide full-scale (100%) output frequency when the S0/1 inputs are both in a logic high state. The light-to-frequency converter circuits, $44_1$-$44_3$, may be individually selected for operation by controlling the logic state of each of the output enable inputs thereof. The control circuit 102 is configured to control each of the light-to-frequency converter circuits, $44_1$-$44_3$, to capture red, green, blue and white light frequency measurement signals during illumination of a corresponding chemically-treated pad 30, 32 or 34 of the test element 16. The control circuit 102 is further configured to pulse-accumulate or integrate each of the red, green, blue and white frequency signals to produce corresponding R, G, B and W signals each corresponding to the exposure, or the amount of light captured, over a given time period. The control circuit 102 is then configured as will be described in greater detail hereinafter, to process the R, G, B and W signals produced by each of the light-to-frequency converter circuits $44_1$-$44_3$ according to a different model to determine a corresponding characteristic of the aqueous solution to which the test element 16 was exposed.

It will be appreciated that the number of radiation detection circuits, $44_1$-$44_3$, may alternatively be configured to detect radiation in other visible and/or non-visible frequency ranges, in a manner consistent with alternate embodiments of the radiation sources, $42_1$-$42_3$, described hereinabove. It will further be appreciated that one or more of the radiation detection circuits, $44_1$-$44_3$, may be provided in the form of a conventional radiation-to-frequency converter, a radiation-to-voltage converter, a radiation-to-count converter, or the like.

It will further be appreciated that the electrical circuitry 100 illustrated in FIG. 5 represents major functional portions of a more detailed electrical circuit that will typically be mounted to the circuit board 40 of FIGS. 2 and 3. One example of such a more detailed electrical circuit is illustrated in U.S. Provisional Patent Application No. 60/836,322 which has been incorporated herein by reference.

Figure 6:
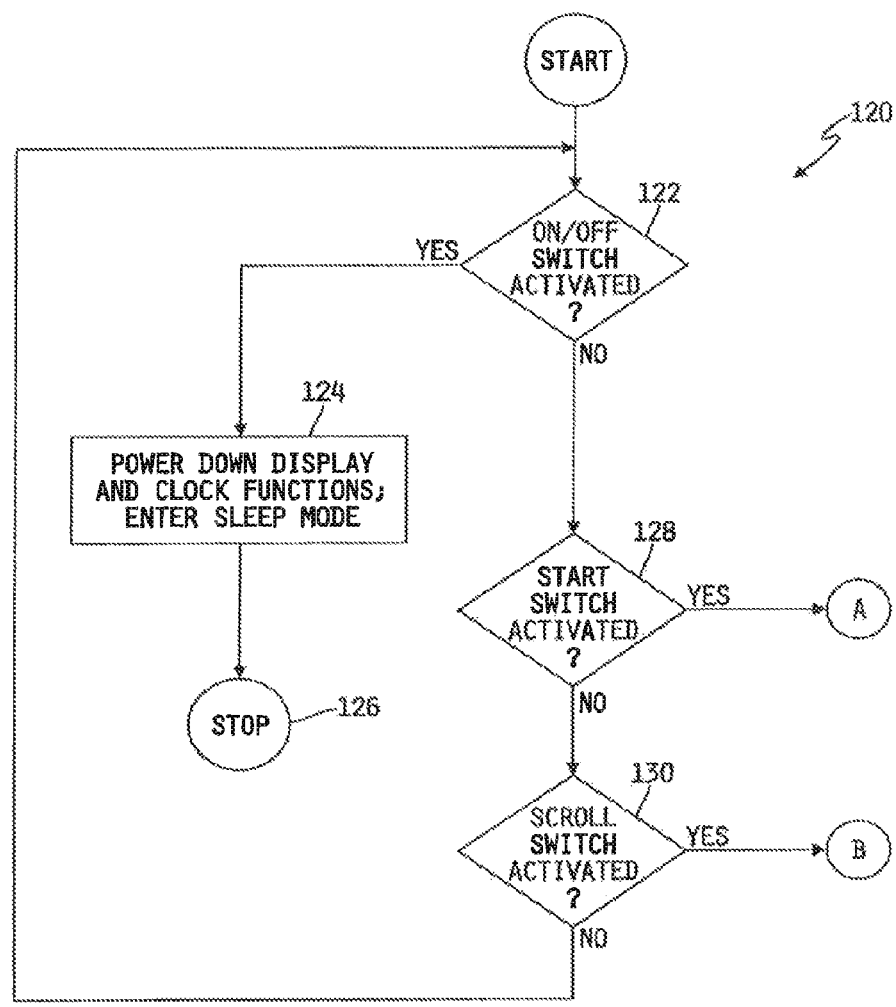
FIG. 6 is a flowchart of one illustrative embodiment of a process for controlling operation of the electronic device of FIGS. 1A and 2-5.

Referring now to FIG. 6, a flow chart is shown of one illustrative embodiment of a process 120 for controlling operation of the electronic device 10 of FIGS. 1A and 2-5. In the illustrated embodiment, the process 120 is stored in the memory unit 115 of the control circuit 102 in the form of instructions that are executable by the control circuit 102 to control operation of the device 10. It will be understood that one or more additional processes may be stored in the memory unit 115 and may be executable by the control circuit 102 to monitor, calibrate, test, and/or control other features and/or operation of the electronic device 10, including, for example, but not limited to, a low battery voltage monitoring function, one or more device calibrations, or the like. In any case, the process 120 will be described herein as being executed by the control circuit 102 pursuant to instructions stored in the memory unit 115.

In the illustrated embodiment, the process 120 begins after the electronic device 10 has concluded a power-up operation resulting from activation of the on/off switch 22 when the electronic device 10 was previously in its off state. The process 120 begins at step 122 where the control circuit 102 is operable to monitor the status of the on/off button 22 to determine whether the on/off button 22 has been activated. If so, the switch 22 has been activated to power down the electronic device 10, and the process execution accordingly advances to step 124 where the control circuit 102 is operable to power down a display unit 18 to deactivate all clock functions and to enter a power-safe "sleep" mode in a conventional manner. Thereafter at step 126, the process 120 stops until the device 10 is powered up again via activation of the on/off switch 22.

If, at step 122, the control circuit 102 determines that the on/off switch has not been activated (following power up of the device 10), process execution advances to step 128 where the control circuit 102 is operable to determine whether the START switch 124 has been activated. If so, process execution advances to subroutine A. If not, process execution advances to step 130 where the control circuit 102 is operable to determine wither the SCROLL switch 24 has been activated. If so, process execution advances to subroutine B, and otherwise process execution loops back to step 122.

Figure 7:
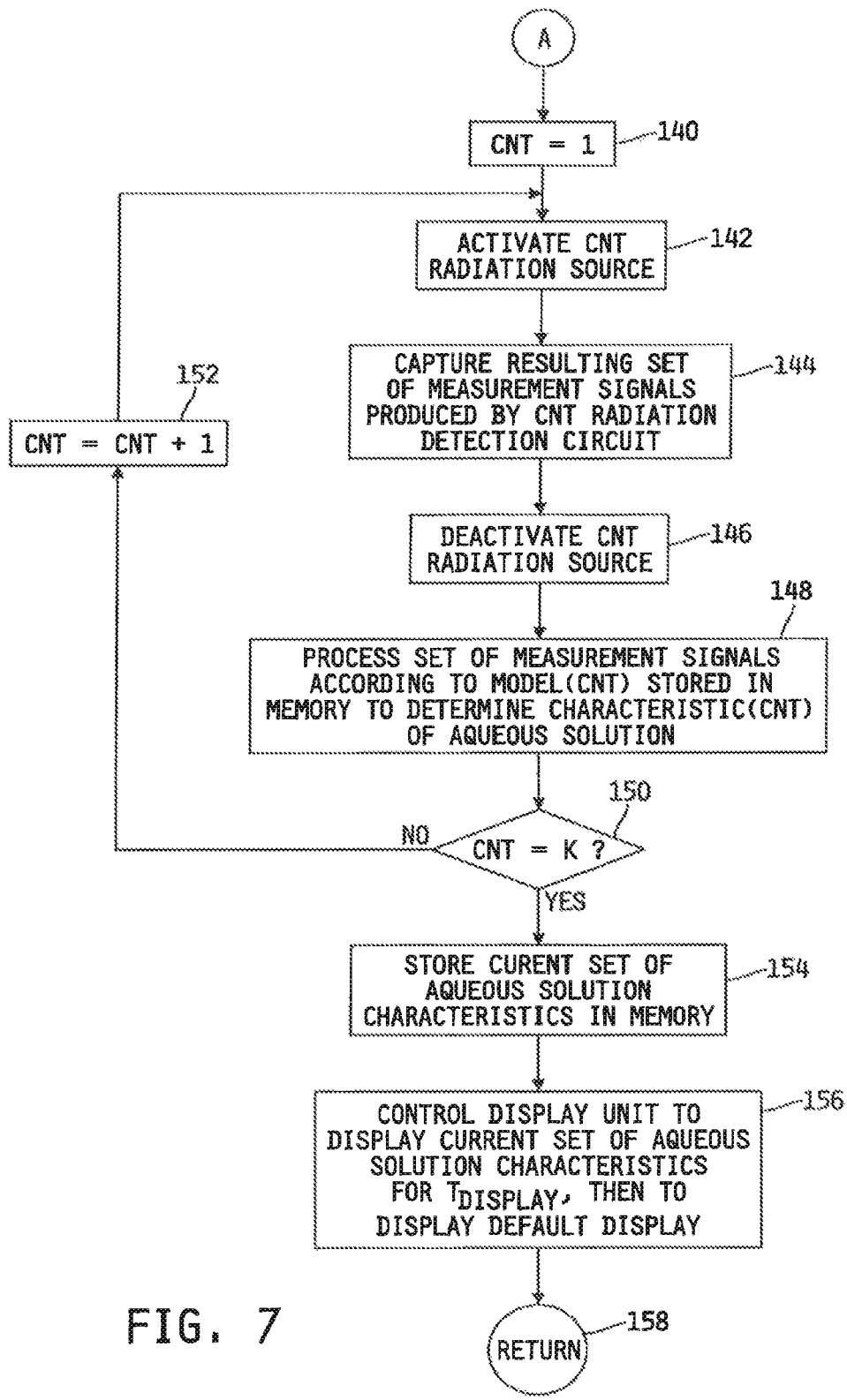
FIG. 7 is a flowchart of one illustrative embodiment of a subroutine that may be called by the process of FIG. 6, for processing information relating to the test element.

Referring now to FIG. 7, a flowchart of one illustrative embodiment of the subroutine A that was called from the "YES" branch of step 128 of the process 120 of FIG. 6, is shown. Subroutine A defines a process for processing a test element 16 received by the electronic device 10 to determine one or more characteristics of an aqueous solution to which the test element 16 has been exposed. Subroutine A begins at step 140 where a count value, CNT, is set equal to one. Thereafter at step 142, the control circuit 102 is operable to activate the radiation source corresponding to CNT. It will be understood that embodiments of the electronic device 10 configured to determine multiple characteristics of an aqueous solution, corresponding radiation source and radiation detection circuit pairs can be activated in any desired sequence to correspondingly determine the multiple characteristics of the aqueous solution in any desired sequence. Accordingly, the numbering of the various radiation source and radiation detection circuit pairs may be random.

In any case, the subroutine A advances from step 142 to step 144 where the resulting set of measurement signals produced by the "CNT" radiation detection circuit in response to irradiation of an appropriate portion of the test element 16 by a corresponding radiation source, as described hereinabove, are captured by the control circuit 102. Thereafter at step 146, the "CNT" radiation source is deactivated by the control circuit 102 as described hereinabove with respect to FIG. 5. Following step 146, subroutine advances to step 148 where the control circuit 102 is operable to process the set of measurement signals just captured according to a "CNT" model that is stored in the memory unit 115 to determine a corresponding "CNT" characteristic of the aqueous solution to which the test element 16 was exposed. Thereafter at step 150, the count value, CNT, is compared to a predefined integer value, K, wherein K corresponds to the total number of characteristics of the aqueous solution to which the test element 16 was exposed that are to be determined by the electronic device 10 pursuant to activation of the START switch 26. In the specific embodiment used throughout this document, for example, K=3. If, at step 150, the count value, CNT, is not equal to K, execution of subroutine A advances to step 152 where the count value, CNT, is incremented by one, and the subroutine A then loops back to step 142.

In the specific example implementation of the electronic device 10 that has been described herein, the aqueous solution may correspond to pool or spa water, and the test element 16 may have three chemically-treated pads 30, 32 and 34 for determining chlorine (or bromine) concentration, total alkalinity, and pH of the pool or spa water, respectively. In this example implementation, CNT=1 may correspond to radiation source $42_1$, radiation detection circuit $44_1$, characteristic 1 may correspond to chlorine (or bromine) concentration, and model 1 may correspond to a chlorine (or bromine) model that is stored in the memory unit 115 and that is configured to map the R, G, B and W signals resulting from operation of the radiation source $42_1$ and the radiation detection circuit $44_1$ to a corresponding chlorine (or bromine) concentration value. CNT=2 and CNT=3 may likewise correspond to like structures and models for determining corresponding alkalinity and pH values.

The subroutine A advances from the "YES" branch of step 150 to step 154 where the control circuit 102 is operable to store the current set of aqueous solution characteristics in the memory unit 115. In the example implementation just described, the set of aqueous solution characteristics correspond to chlorine (or bromine), alkalinity and pH values of pool or spa water, although it will be understood that a set of one or more aqueous solution characteristics may correspond to one or more additional or alternative aqueous solution characteristics of the type described herein. Additionally, although not specifically illustrated in FIG. 7, the control circuit 102 may be further operable at step 154 to store date and/or time values along with the set of aqueous solution characteristics in the memory unit 115, corresponding to the calendar date and/or time of day at which the set of aqueous solution characteristics were determined.

From step 154, the subroutine A advances to step 156 where the control circuit 102 is operable to control the display unit 18 to display the current set of aqueous solution characteristics for a predetermined time period, $T_{DISPLAY}$, and to then display a default display. $T_{DISPLAY}$ may be any desired time period, and the default display may be any desired display including, for example, but not limited to, a conventional power-saving display, a conventional screen-saver display, a company logo display or the like. In any case, execution of the subroutine A advances from step 156 to step 158 where the subroutine A is returned to step 128 of the process 120 of FIG. 6.

Figure 8:
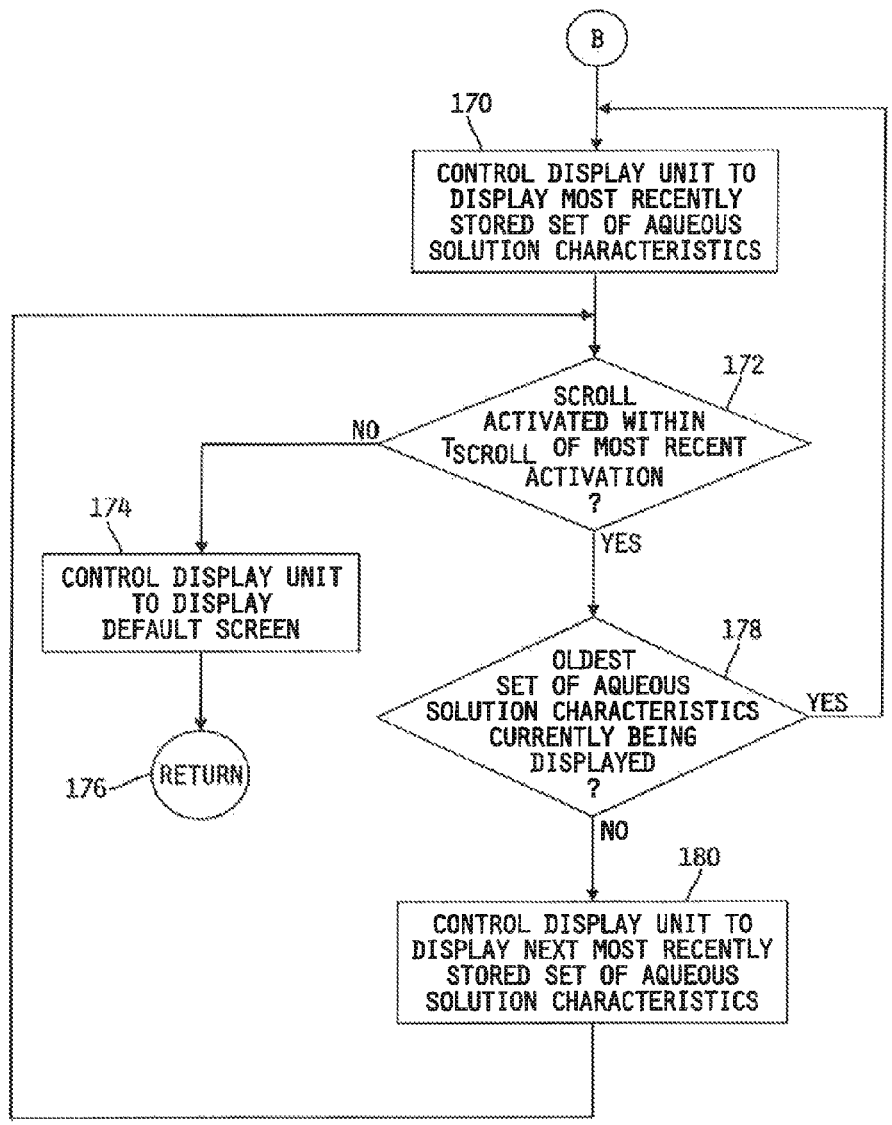
FIG. 8 is a flowchart of one illustrative embodiment of data scrolling subroutine that may be called by the process of FIG. 7.

Referring now to FIG. 8, a flowchart of one illustrative embodiment of the subroutine B that was called from the "YES" branch of step 130 of the process 120 of FIG. 6 is shown. The memory unit 115 of the control circuit 102 may be configured to store any number of sets of aqueous solution characteristics that may be scrolled through via successive activations of the scroll switch 24, and the control circuit 102 is operable to control such scrolling, in one embodiment, in accordance with the subroutine B of FIG. 8. The subroutine B begins at step 170 where the control circuit 102 is operable to control the display unit 18 to display the most recently stored set of aqueous solution characteristics. Thereafter at step 172, the control circuit 102 is operable to determine whether the scroll switch 24 has been activated within a time period, $T_{SCROLL}$, of the most recent activation of the scroll switch 26. The time period $T_{SCROLL}$ may be any desired time period, and if the control circuit 102 determines at step 172 that the scroll switch 24 has not been activated within $T_{SCROLL}$ of the most recent activation of the scroll switch 24, execution of the subroutine B advances to step 174 where the control circuit 102 is operable to control the display unit 18 to display the default screen as described hereinabove. Thereafter at step 176, execution of the subroutine B is returned to step 130 of the process 120 of FIG. 6.

If, at step 172, the control circuit 102 determines that the scroll switch 24 has been activated within $T_{SCROLL}$ of the most recent activation of the scroll switch 24, execution of the subroutine B advances to step 178 where the control circuit 102 is operable to determine whether the current set of aqueous solution characteristics being displayed on the display unit 18 corresponds to the oldest set of aqueous solution characteristics stored in the memory unit 115. If so, execution of the subroutine B loops back to step 170 to display the most recently stored set of aqueous solution characteristics. If, however, the control circuit 102 determines at step 178 that the set of aqueous solution characteristics currently being displayed is not the oldest set of aqueous solution characteristics stored in the memory unit 115, execution of the subroutine B advances to step 180 where the control circuit 102 is operable to control the display unit 18 to display the next most recently stored set of aqueous solution characteristics. From step 180, execution of the subroutine B loops back to step 172.

In one illustrative implementation of the electronic device 10, the memory unit 115 is configured to store L sets of aqueous solution characteristics, where L may be any positive integer. By successive activations of the scroll switch 24, each within the time period $T_{SCROLL}$ of the last activation of the scroll switch 24, the L sets of aqueous solution characteristics stored in the memory unit 115 are sequentially displayed beginning with the most recently stored set of aqueous solution characteristics and stepping sequentially to the oldest stored set of aqueous solution characteristics. When the last, or oldest, set of aqueous solution characteristics is displayed, the next activation of the scroll switch 24 will cause the most recently stored set of aqueous solution characteristics to be displayed. As new sets of aqueous solution characteristics are stored in the memory unit 115, the last, or oldest, sets of aqueous solution characteristics are overwritten so as to maintain only the most recent L sets aqueous solution characteristics stored in the memory unit 115. In one exemplary embodiment, L=9, although other values of L are contemplated. It will be appreciated that the memory unit 115 may alternatively be configured to store more or fewer sets of aqueous solution characteristics, and/or that the subroutine B may be modified to accomplish other scrolling strategies. Any such modifications to the subroutine B would be a mechanical step for a skilled programmer.

Referring again to FIG. 7, step 148 of the subroutine A comprises processing the set of measurement signals according to a particular model stored in the memory unit 115 to determine a corresponding characteristic of the aqueous solution to which a test element 16 has been exposed. Such a model may be provided in the form of one or more equations, graphs, tables or the like, and in one exemplary embodiment of the electronic device 10, three such models are provided with each such model comprising multiple equations.

Figure 9:
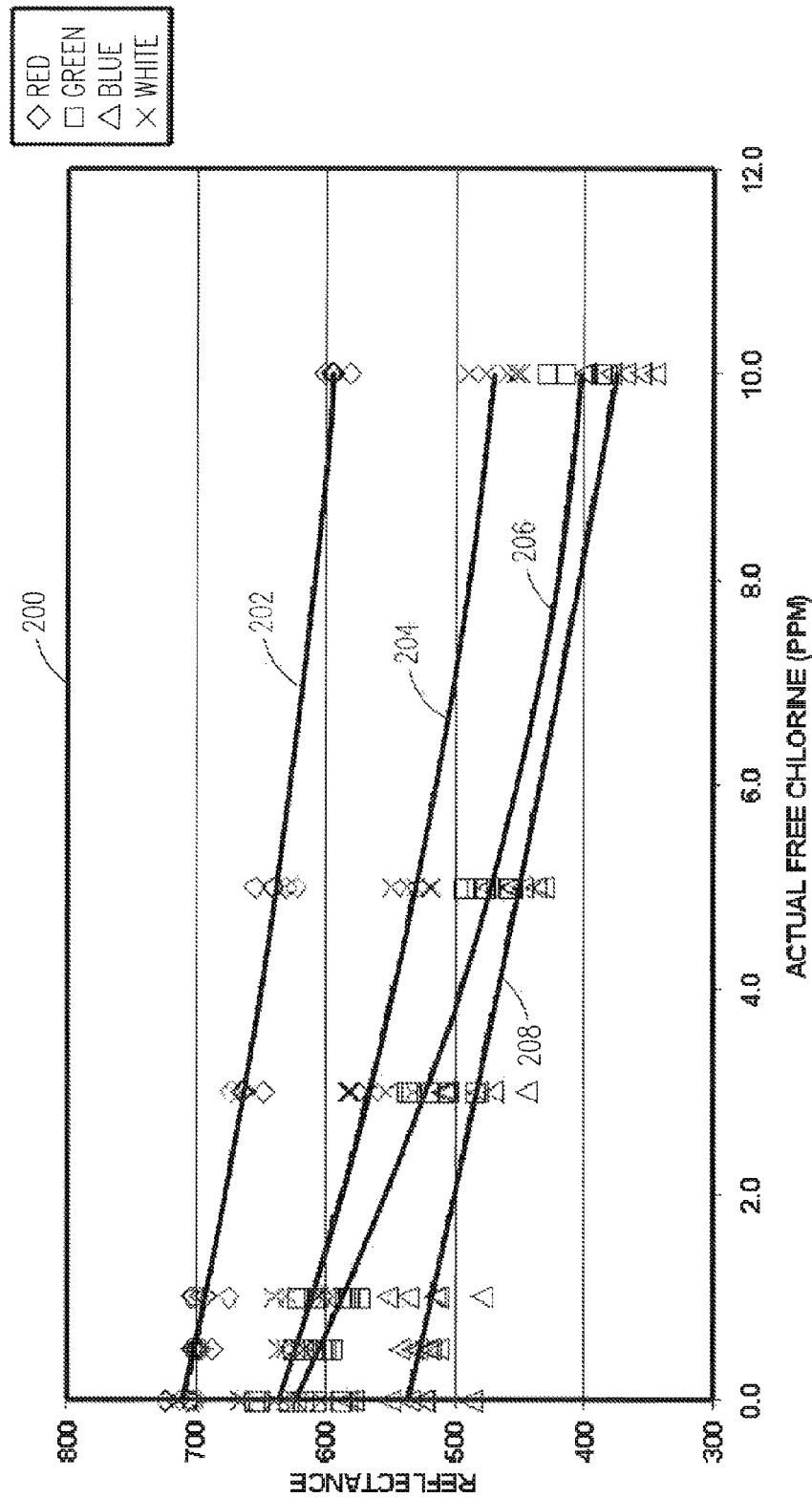
FIG. 9 is plot of reflectance values vs. free chlorine values illustrating a typical distribution of four color components of a free chlorine test portion of the test element of FIG. 1B over a range of free chlorine values as measured by the device of FIGS. 1A and 2-5.

Referring now to FIG. 9, a plot 200 is shown of reflectance values vs. actual free chlorine concentration for a number of control samples each having a different known free chlorine concentration value. The plot 200 illustrates the measurement signals produced by one of the radiation detection circuits described hereinabove in the form of Red, Green, Blue and White frequency components. The Red, or R, frequency component of the number of aqueous solution samples is represented by small diamonds having a curve 202 approximately fitted thereto. The White, or W, frequency component is illustrated by small x's having a curve 204 approximately fitted thereto. The Green, or G, frequency components are illustrated by small squares having a curve 206 approximately fitted thereto, and the Blue, or B, frequency components are represented by small triangles having a curve 208 approximately fitted thereto. In the plot 200 of FIG. 9, the R, G, B and W values represent ratios of frequency count values of the measured signals relative to a corresponding frequency count value of a calibration strip. Thus, for example, the R values represent ratios of measured R frequency values, in units of Hz, and an R frequency value, in units of Hz, of a calibration strip, e.g., a white calibration strip. The G, B and W values in the plot 200 of FIG. 9 represent similar ratios.

Figure 10:
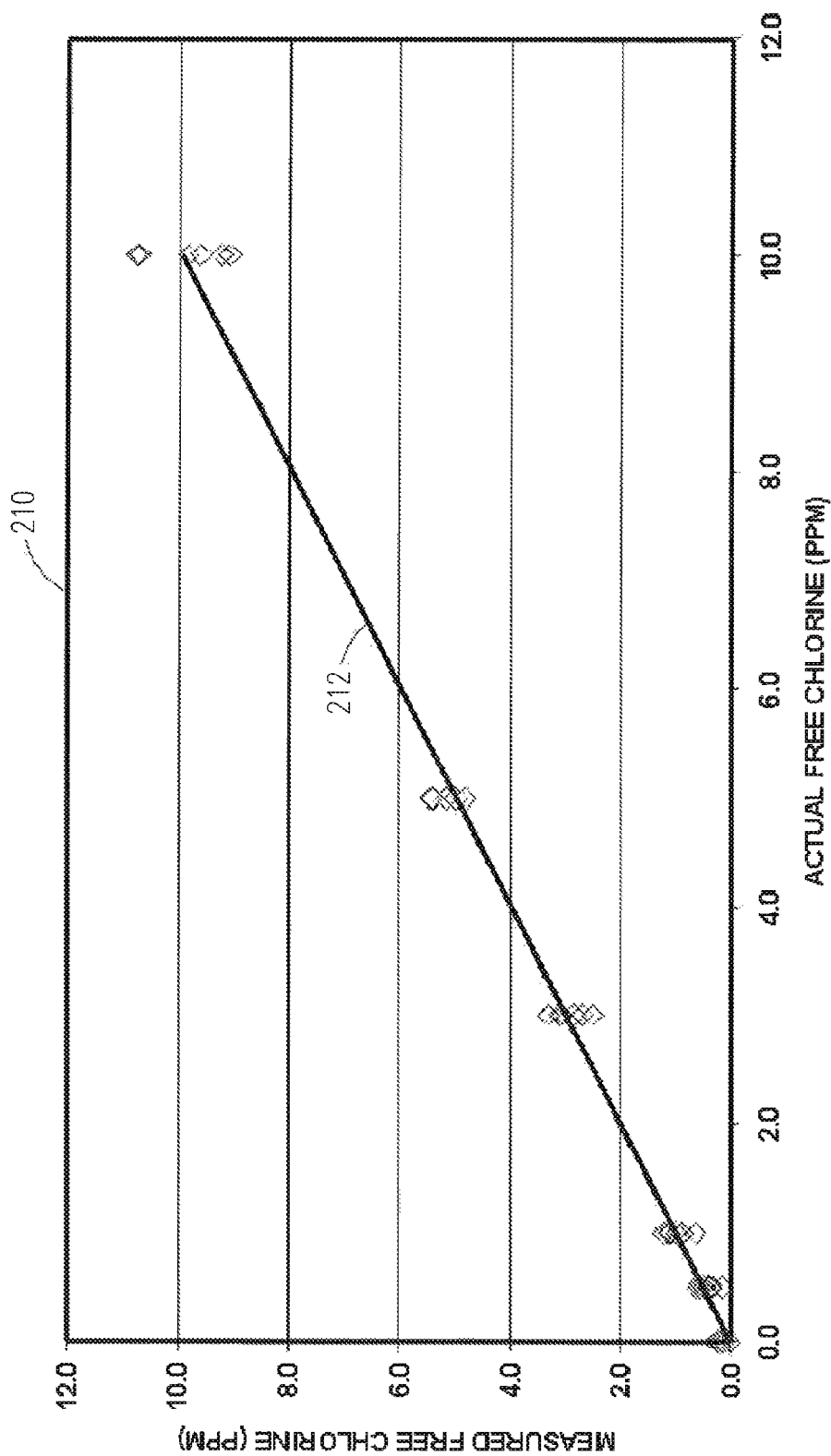
FIG. 10 is a plot of free chlorine values measured by the device of FIGS. 1A and 2-5 vs. actual free chlorine values of a number of aqueous solutions each having known chlorine concentration.

In the illustrated embodiment, the data in the plot 200 is used to form a 2-equation model for chlorine as a function of R, G, B and W. A first equation is of the form $ALG=(a*R+b*G+c*B+d*W)*R^e*G^f*B^g*W^h$, where a-h are constants. For the example data illustrated in FIG. 9, a=−0.281240, b=−1.454026, c=−0.20798, d=1.906914, e=−0.83526, f=1.829174, g=−1.78626 and h=0.653039. A second equation is of the form $MFCI=w*ALG^3+x*ALG^2+y*ALG+z$, where w-z are constants. For the example data illustrated in FIG. 9, w=0.006304, x=−0.064922, y=0.422585 and z=0.483674. In the operation of the system 10, the processor 102 is operable to process each set of R, G, B and W signals produced by the radiation detection circuit(s) according to the foregoing model to determine the free chlorine value of the aqueous solution to which the test element 16 has been exposed, and to display the result on the display unit 18. FIG. 10 is a plot 210 of the measured free chlorine values, MFCI, resulting from the free chlorine model, as measured by the device 10 of FIGS. 1A and 2-5, vs. the corresponding actual free chlorine values of the various aqueous solution control samples. The MFCI values are represented by small diamonds having a curve 212 approximately fitted thereto.

The first and second equations of the above free chlorine model define one embodiment of the free chlorine model that is stored in the memory unit 115. It will be understood that the forms of these first and second equations, as well as the example values of the various constants in these equations, are provided only for illustrative purposes, and alternate forms of the first and second equations and of any constants used therein are contemplated by this disclosure.

Figure 11:
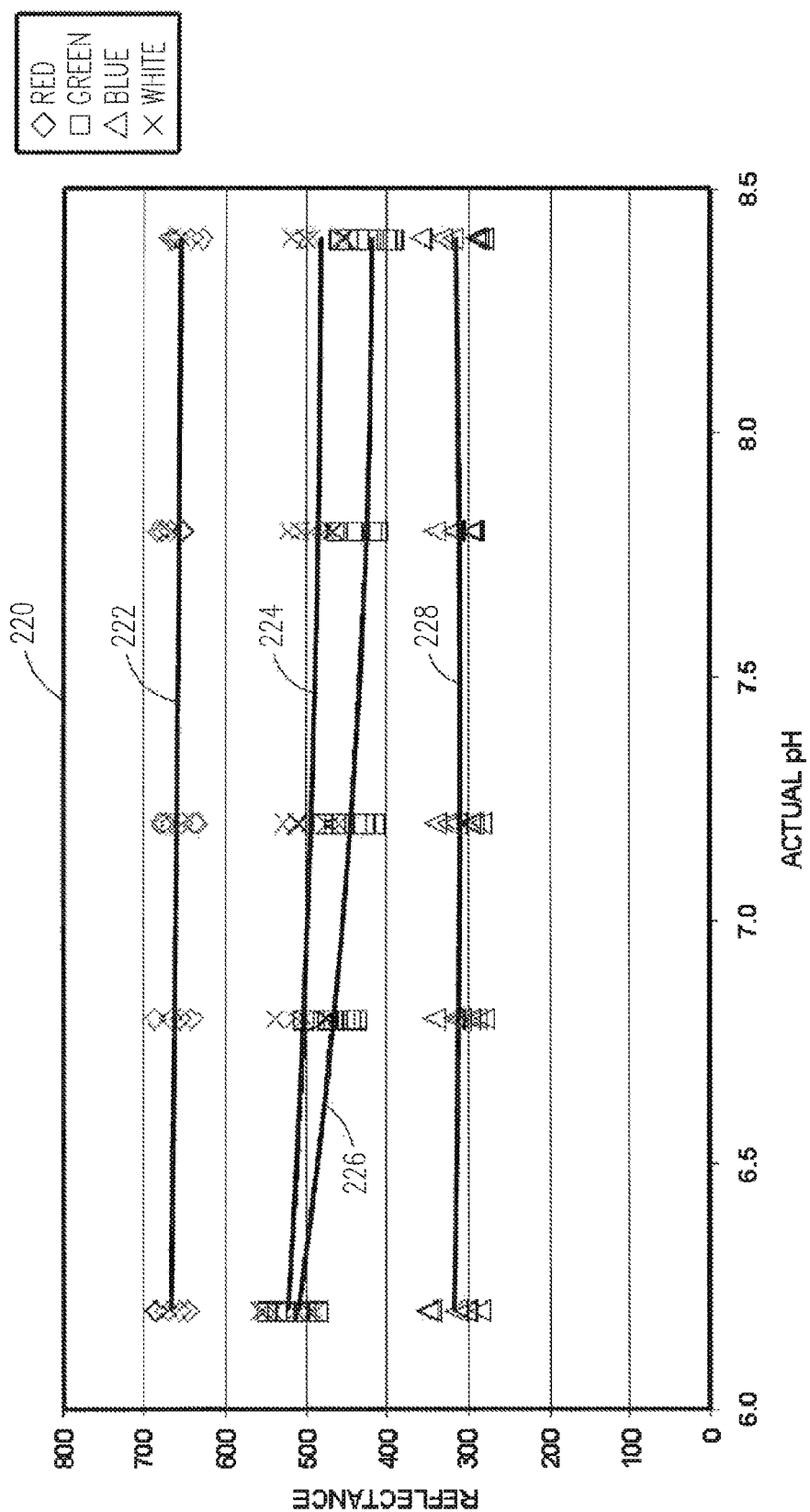
FIG. 11 is plot of reflectance values vs. relative pH values illustrating a typical distribution of four color components of a pH test portion of the test element of FIG. 1B over a range of relative pH values as measured by the device of FIGS. 1 and 3-5.

Referring now to FIG. 11, a plot 220 is shown of reflectance values vs. actual pH for a number of control samples each having a different known pH value. The plot 220 illustrates the measurement signals produced by one of the radiation detection circuits described hereinabove in the form of Red, Green, Blue and White frequency components. The Red, or R, frequency component of the number of aqueous solution samples is represented by small diamonds having a curve 222 approximately fitted thereto. The White, or W, frequency component is illustrated by small x's having a curve 224 approximately fitted thereto. The Green, or G, frequency components are illustrated by small squares having a curve 226 approximately fitted thereto, and the Blue, or B, frequency components are represented by small triangles having a curve 228 approximately fitted thereto. In the plot 220 of FIG. 11, the R, G, B and W values represent ratios of frequency count values of the measured signals relative to a corresponding frequency count value of a calibration strip, as described hereinabove with respect to FIG. 9.

Figure 12:
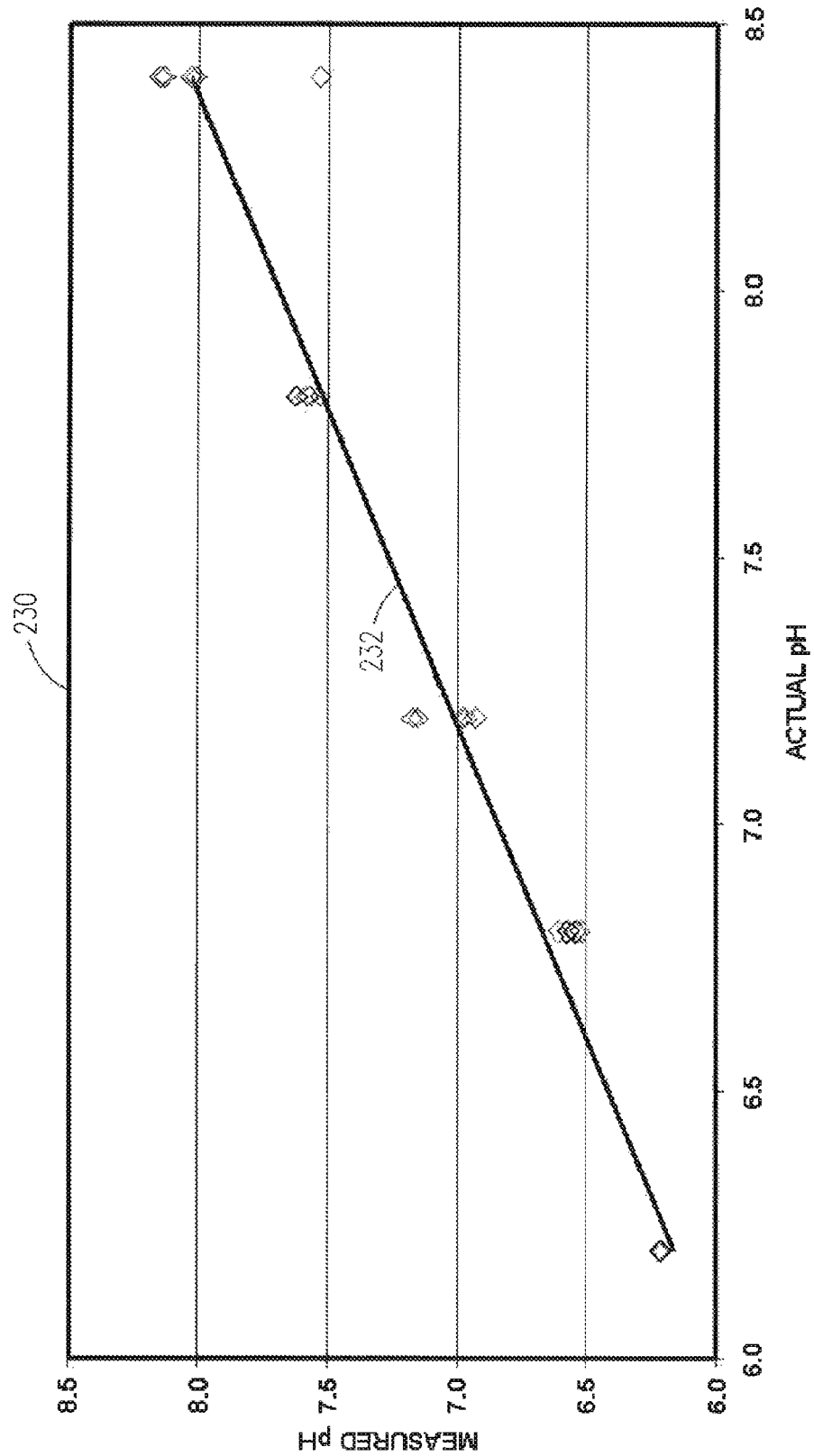
FIG. 12 is a plot of relative pH values measured by the device of FIGS. 1A and 2-5 vs. actual pH values of a number of controlled aqueous solutions each having known pH values.

In the illustrated embodiment, the data in the plot 220 is used to form a 2-equation model for pH as a function of R, G, B and W. A first equation is of the form $ALG=(a*R+b*G+c*B+d*W)*R^e*G^f*B^g*W^h$, where a-h are constants. For the example data illustrated in FIG. 11, a=0.531448, b=−1.9864, c=1.20228, d=0.52574, e=−3, f=−2, g=2 and h=0.574138. A second equation is of the form $MpH=w*(ALG*10^5)^3+x*(ALG*10^5)^2+y*(ALG*10^5)+z$, where w-z are constants. For the example data illustrated in FIG. 11, w=−1.4315, x=3.0284, y=0.1661 and z=6.2109. In the operation of the system 10, the processor 102 is operable to process each set of R, G, B and W signals produced by the radiation detection circuit(s) according to the foregoing model to determine the pH value of the aqueous solution to which the test element 16 has been exposed, and to display the result on the display unit 18. FIG. 12 is a plot 230 of the measured pH values, MpH, resulting from the pH model, as measured by the device 10 of FIGS. 1A and 2-5, vs. the corresponding actual pH values of the various aqueous solution control samples. The MpH values are represented by small diamonds having a curve 232 approximately fitted thereto.

The first and second equations of the above pH model define one embodiment of the pH model that is stored in the memory unit 115. It will be understood that the forms of these first and second equations, as well as the example values of the various constants in these equations, are provided only for illustrative purposes, and alternate forms of the first and second equations and of any constants used therein are contemplated by this disclosure.

Figure 13:
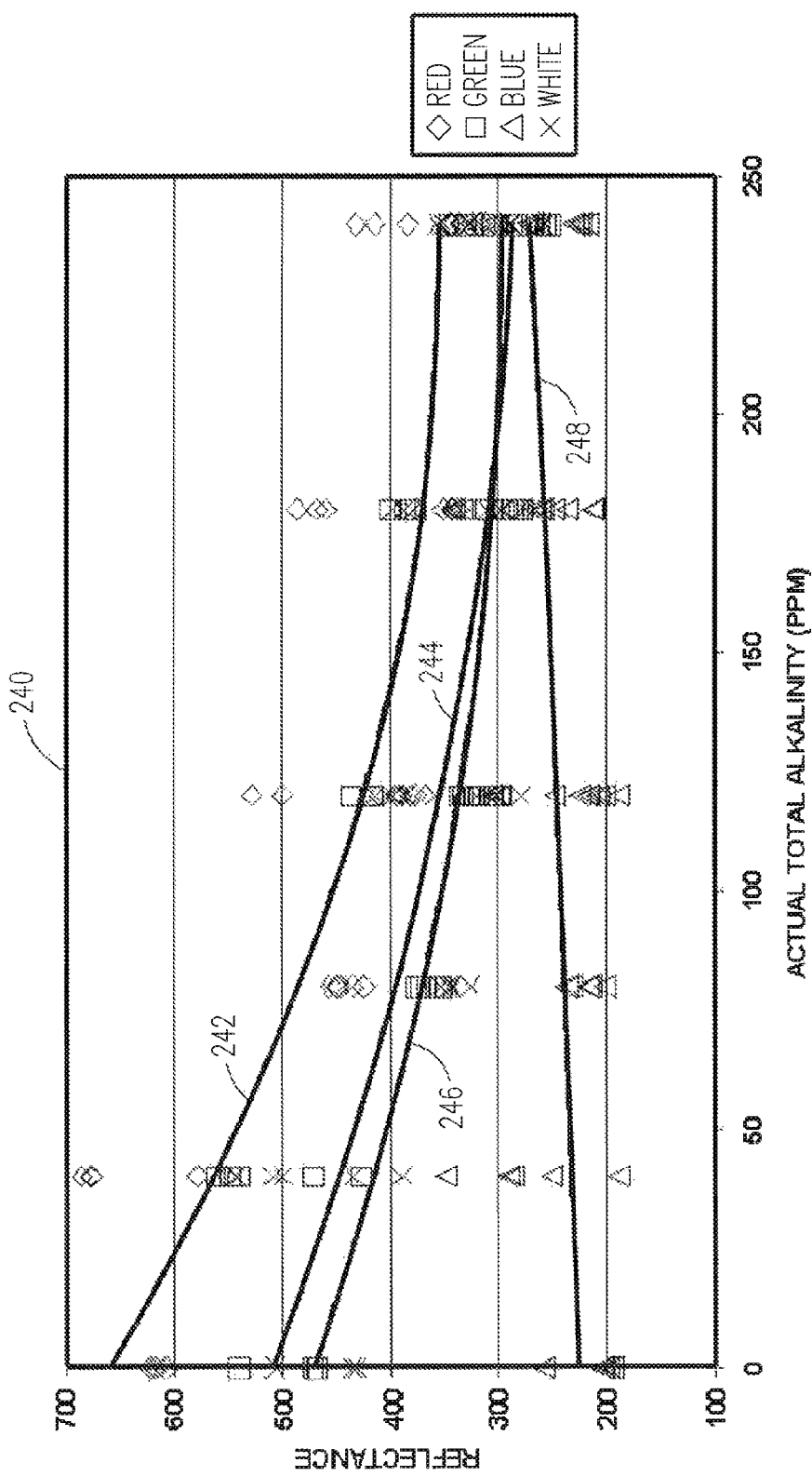
FIG. 13 is plot of reflectance values vs. total alkalinity values illustrating a typical distribution of four color components of an alkalinity test portion of the test element of FIG. 1B over a range of total alkalinity values as measured by the device of FIGS. 1A and 2-5.

Referring now to FIG. 13, a plot 240 is shown of reflectance values vs. actual total alkalinity for a number of control samples each having a different known alkalinity value. The plot 240 illustrates the measurement signals produced by one of the radiation detection circuits described hereinabove in the form of Red, Green, Blue and White frequency components. The Red, or R, frequency component of the number of aqueous solution samples is represented by small diamonds having a curve 242 approximately fitted thereto. The Green, or G, frequency component is illustrated by small squares having a curve 244 approximately fitted thereto. The white, or W, frequency components are illustrated by small x's having a curve 246 approximately fitted thereto, and the Blue, or B, frequency components are represented by small triangles having a curve 248 approximately fitted thereto. In the plot 240 of FIG. 13, the R, G, B and W values represent ratios of frequency count values of the measured signals relative to a corresponding frequency count value of a calibration strip, as described hereinabove with respect to FIG. 9.

Figure 14:
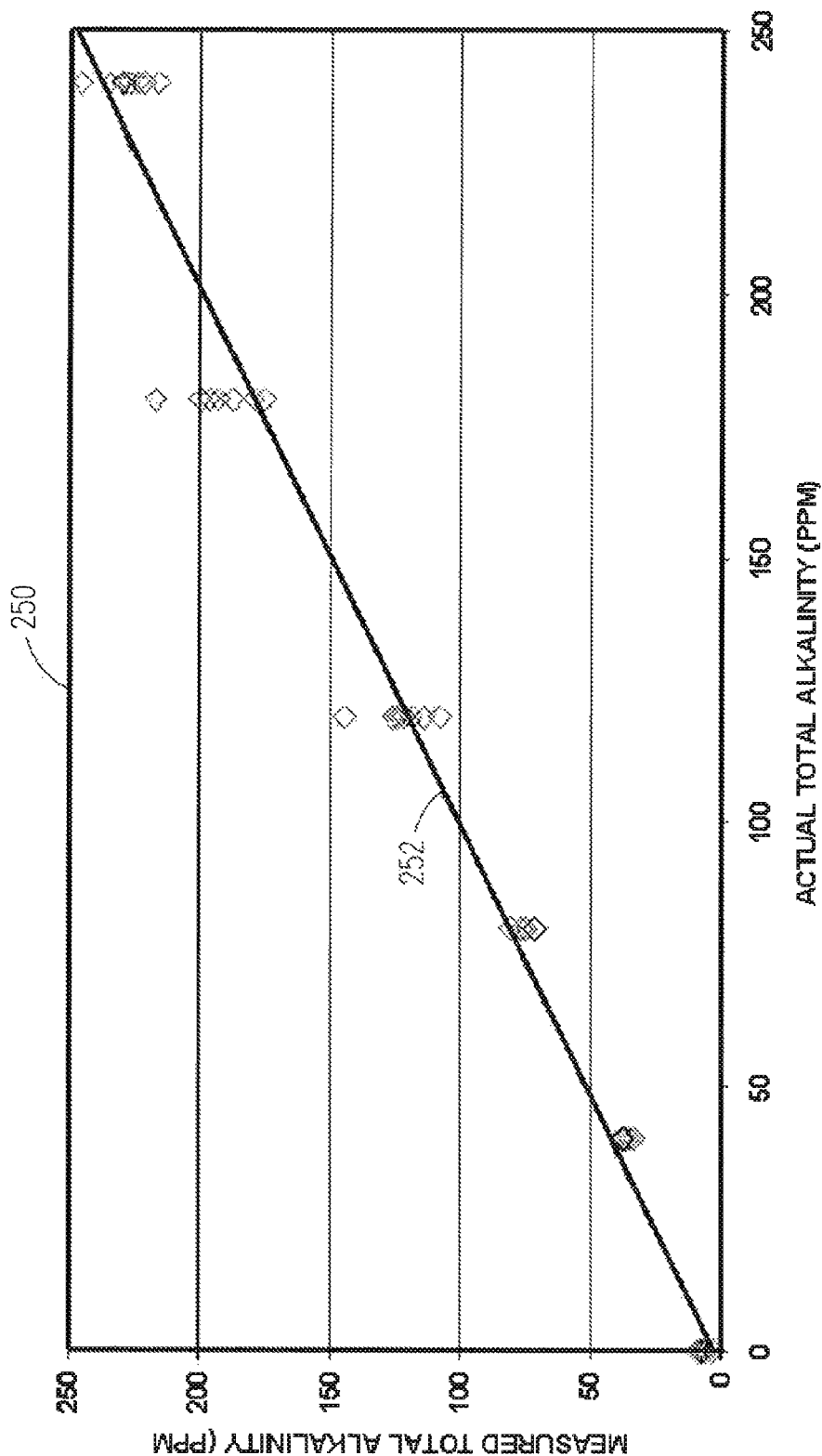
FIG. 14 is a plot of total alkalinity values measured by the device of FIGS. 1A and 2-5 vs. actual total alkalinity values of a number of aqueous solutions each having known total alkalinity values.

In the illustrated embodiment, the data in the plot 240 is used to form a 2-equation model for total alkalinity as a function of R, G, B and W. A first equation is of the form $ALG=(a*W+b*R+c*G+d*B)*W^e*R^f*G^g*B^h$, where a-h are constants. For the example data illustrated in FIG. 13, a=−1.88019, b=0.202251, c=1.188813, d=−0.70284, e=−2.06506, f=−0.05257, g=1.885299 and h=−0.73126. A second equation is of the form $MALK=x*ALG^2+y*ALG+z$, where x-z are constants. For the example data illustrated in FIG. 11, x=−2367.2, y=−5822.9 and z=−3290.9. In the operation of the system 10, the processor 102 is operable to process each set of R, G, B and W signals produced by the radiation detection circuit(s) according to the foregoing model to determine the total alkalinity value of the aqueous solution to which the test element 16 has been exposed, and to display the result on the display unit 18. FIG. 14 is a plot 250 of the measured total alkalinity values, MALK, resulting from the total alkalinity model, as measured by the device 10 of FIGS. 1A and 2-5, vs. the corresponding actual total alkalinity values of the various aqueous solution control samples. The MALK values are represented by small diamonds having a curve 252 approximately fitted thereto.

The first and second equations of the above pH model define one embodiment of the pH model that is stored in the memory unit 115. It will be understood that the forms of these first and second equations, as well as the example values of the various constants in these equations, are provided only for illustrative purposes, and alternate forms of the first and second equations and of any constants used therein are contemplated by this disclosure.

While the invention has been illustrated and described in detail in the foregoing drawings and description, the same is to be considered as illustrative and not restrictive in character, it being understood that only illustrative embodiments thereof have been shown and described and that all changes and modifications that come within the spirit of the invention are desired to be protected.

What is claimed is:

1. A device for analyzing a plurality of characteristics of an aqueous solution, comprising:
a portable hand-held housing having an interior;
a test element receiving port configured to receive a wetted test element;
circuitry in the housing for selectively generating radiation for interrogating a plurality of different portions of a wetted test element when placed within the test element receiving port, for receiving radiation reflected from the test element, and for generating a display responsive to the reflected radiation and indicative of the plurality of different characteristics of the aqueous solution; and,
wherein the test element receiving port is proximate portions of the circuitry generating the radiation and receiving the reflected radiation and the radiation-transmissive test element receiving port comprises:
a slot formed in the housing proximate portions of the circuitry generating the radiation and receiving the reflected radiation;
a radiation-transmissive test element placement member attached to the housing toward a bottom of the slot, closing the slot and isolating an interior of the housing and the circuitry from an exterior of the housing while permitting the generated radiation to pass out of the housing and the reflected radiation to pass back into the housing.

2. The device of claim 1, wherein the circuitry is configured to execute instructions in response to measurement signals generated upon detection of reflected radiation to determine the different characteristics of the aqueous solution in response to the reflected radiation received by the radiation detection circuits.

3. The device of claim 2, further comprising a switch,
wherein the circuitry is operable, according to the instructions, to be responsive to activation of the switch to display a set of values of the plurality of different characteristics of the aqueous solution.

4. The device of claim 3, wherein the control circuit is operable, according to the instructions, to be responsive to multiple activations of the switch to sequentially display different sets of values of the plurality of different characteristics of the aqueous solution.

5. The device of claim 2, further comprising a switch,
wherein the circuitry is operable, according to the instructions, to be responsive to activation of the switch to process each of the plurality of different signals to determine the corresponding plurality of different characteristics of the aqueous solution.

6. The device of claim 1, further comprising a display on the housing and the display being associated with the circuitry and displaying an indication responsive to the determined different characteristic of the aqueous solution.

7. The device of claim 1, wherein the circuitry comprises:
a plurality of radiation sources within the housing;
a plurality of radiation detection circuits within the housing, wherein each radiation detection circuit is associated with a corresponding radiation source to detect radiation reflected from a test element and each radiation detection circuit being associated with a different characteristic of the aqueous solution;
wherein each radiation detection circuit is configured to generate one or more measurement signals indicative of the associated different characteristic of the aqueous solution.

8. The device of claim 7, further comprising a radiation guide member disposed between the test element receiving port and the circuitry.

9. The device of claim 8, wherein the radiation guide member directs radiation along a first set of paths from the circuitry and along a second set of paths from the test element and test element receiving port toward the radiation detection circuits, and
wherein the radiation guide member minimizes light transmission between the first and second paths.

10. The device of claim 9, wherein each radiation source includes a light generating element, and each radiation detection circuit includes a light detector and the radiation guide member comprises:
a plurality of first cavities each receiving a respective light generating element;
a plurality of second cavities each receiving a respective light detector; and
a wall separating the first and second cavities effective to minimize light transmission there between.

11. The device of claim 10, wherein the radiation guide member comprises:
a plurality of first passageways each extending from a respective first cavity to provide light communication between the light generating element and the test element receiving port; and
a plurality of second passageways each extending from a respective second cavity to provide light communication between the test element receiving port and a respective light detector.

12. The device of claim 11, further comprising:
each first passageway defining a first central axis therethrough;
each second passageway defining a second axis therethrough; and,
wherein each second axis is disposed at an acute angle to a corresponding first axis.

13. The device of claim 7, wherein the circuitry includes a control circuit that processes each of the measurement signals according to a corresponding one of a plurality of models relating a different one of the plurality of signals to a corresponding one of the plurality of different characteristics of the aqueous solution to determine a corresponding one of the plurality of different characteristics of the aqueous solution.

14. The device of claim 7, wherein each of the plurality of radiation detection circuits comprises circuitry producing a set of color signals relating to a color of different color portions of the test element, the color of each of the different color portions of the test element resulting from exposure to the aqueous solution.

15. The device of claim 14, wherein the plurality of different characteristics of the aqueous solution include chlorine concentration, pH level and alkalinity concentration, and wherein the circuitry further comprises first, second and third models, the first model relating a first set of color signals produced by a first one of the plurality of radiation detection circuits to chlorine concentration values, the second model relating a second set of color signals produced by a second one of the plurality of radiation detection circuits to pH level values, and the third model relating a third set of color signals produced by a third one of the plurality of radiation detection circuits to alkalinity concentration values.

16. The device of claim 1, wherein the plurality of different characteristics of the aqueous solution include one or more of chlorine concentration, bromine concentration, pH level, alkalinity concentration, ammonia concentration, nitrite concentration, nitrate concentration, solution hardness, peracetic acid concentration, peroxide concentration and chloramine concentration.

17. A device for analyzing characteristics of an aqueous solution, comprising:
a portable hand-held housing having an interior;
a test element receiving port configured to receive a wetted test element;
a plurality of radiation sources within the housing arranged to transmit radiation through a plurality of different spaced apart portions of a test element receiving port;
a plurality of radiation detection circuits within the housing, wherein each radiation detection circuit is associated with a corresponding radiation source to detect radiation reflected from a corresponding portion of a test element and each radiation detection circuit being associated with a different characteristic of the aqueous solution;
wherein each radiation detection circuit is configured to generate one or more measurement signals indicative of the associated different characteristic of the aqueous solution in response to detected, reflected radiation;
a control circuit disposed within the housing and associated with the radiation detection circuits for determining the different characteristics of the aqueous solution based at least in part on the measurement signals;
wherein the test element receiving port is proximate portions of the radiation sources and radiation detection circuits, and the radiation-transmissive test element receiving port comprises:
a slot formed in the housing proximate portions of the radiation sources and radiation detection circuits; and,
a radiation-transmissive test element placement member attached to an underside of the housing juxtaposition to the slot thereby closing the slot and isolating the interior of the housing including the radiation sources, radiation detection circuits and control circuit from an exterior of the housing while permitting the generated radiation to pass out of the housing and the reflected radiation to pass back into the housing.

18. The device of claim 17, wherein the control circuit is configured to execute instructions to process the measurement signals from the radiation detection circuits to determine the different characteristics of the aqueous solution in response to the reflected radiation received by the radiation detection circuits.

19. The device of claim 18, further comprising a display on the housing and the display being associated with the control circuit and displaying an indication responsive to the determined different characteristic of the aqueous solution.

20. The device of claim 17, wherein the slot is at least partially defined by a pair of opposed walls of the housing, with the walls extending outwardly from and juxtaposed about the test element placement member.

21. The device of claim 17, wherein the plurality of different characteristics of the aqueous solution include one or more of chlorine concentration, bromine concentration, pH level, alkalinity concentration, ammonia concentration, nitrite concentration, nitrate concentration, solution hardness, peracetic acid concentration, peroxide concentration and chlorainine concentration.

* * * * *